(12) United States Patent
Cryder et al.

(10) Patent No.: US 10,463,405 B2
(45) Date of Patent: *Nov. 5, 2019

(54) DEVICES AND METHODS FOR INSERTING A VERTEBRAL FIXATION MEMBER

(71) Applicant: GLOBUS MEDICAL, INC., Audubon, PA (US)

(72) Inventors: Joel Cryder, Warrington, PA (US); Matthew Bechtel, Philadelphia, PA (US); Andrew Iott, Newtown Square, PA (US); Edward Karpowicz, Sewell, NJ (US); Douglas Cahill, Lititz, PA (US); Robert Rightler, Pennsburg, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/662,995

(22) Filed: Jul. 28, 2017

(65) Prior Publication Data

US 2018/0008324 A1    Jan. 11, 2018

Related U.S. Application Data

(63) Continuation of application No. 14/516,631, filed on Oct. 17, 2014, now Pat. No. 9,750,545, which is a continuation of application No. 12/413,058, filed on Mar. 27, 2009, now Pat. No. 8,900,238.

(51) Int. Cl.
*A61B 17/70* (2006.01)
*A61B 17/02* (2006.01)

(52) U.S. Cl.
CPC ...... *A61B 17/7085* (2013.01); *A61B 17/7004* (2013.01); *A61B 17/708* (2013.01); *A61B 17/7086* (2013.01); *A61B 17/0206* (2013.01)

(58) Field of Classification Search
CPC .............. A61B 17/708; A61B 17/7083; A61B 17/7085; A61B 17/7086
See application file for complete search history.

(56) References Cited

U.S. PATENT DOCUMENTS

| | | | |
|---|---|---|---|
| 5,005,562 A | 4/1991 | Cotrel | |
| 5,181,917 A | 1/1993 | Rogozinski | |
| 5,261,909 A | 11/1993 | Sutterlin et al. | |
| 5,415,659 A | 5/1995 | Lee et al. | |
| 5,487,744 A | 1/1996 | Howland | |
| 5,540,688 A | 7/1996 | Navas | |
| 5,591,166 A | 1/1997 | Bernhardt et al. | |
| 5,603,714 A | 2/1997 | Kaneda et al. | |
| 6,063,089 A | 5/2000 | Errico et al. | |

(Continued)

FOREIGN PATENT DOCUMENTS

| | | |
|---|---|---|
| WO | 199514437 A1 | 6/1995 |
| WO | 2001028436 A1 | 4/2001 |
| WO | 2007059207 A2 | 5/2007 |

*Primary Examiner* — Jacqueline T Johanas

(57) ABSTRACT

Devices, systems, and methods for inserting a vertebral stabilization member, such as a rod. The insertion device includes an outer guide tube, a pin assembly including a pin and a pusher member extending therethrough. The insertion device is configured to actuate a rod between a first orientation and a second orientation angled with respect to the first orientation in order to position the rod in an appropriate location for attachment to bone.

9 Claims, 30 Drawing Sheets

(56) References Cited

U.S. PATENT DOCUMENTS

| | | |
|---|---|---|
| 6,132,432 A | 10/2000 | Richelsoph |
| 6,226,548 B1 | 5/2001 | Foley et al. |
| 6,245,072 B1 | 6/2001 | Zdeblick et al. |
| 6,280,442 B1 | 8/2001 | Barker et al. |
| 6,287,311 B1 | 9/2001 | Sherman et al. |
| 6,443,953 B1 | 9/2002 | Perra et al. |
| 6,485,494 B1 | 11/2002 | Haider |
| 6,530,929 B1 | 3/2003 | Justis et al. |
| 6,641,586 B2 | 11/2003 | Varieur |
| 6,648,888 B1 | 11/2003 | Shluzas |
| 6,740,086 B2 | 5/2004 | Richelsoph |
| 6,755,829 B1 | 6/2004 | Bono et al. |
| 6,790,209 B2 | 9/2004 | Beale et al. |
| 6,843,791 B2 | 1/2005 | Serhan |
| 7,083,621 B2 | 8/2006 | Shaolian et al. |
| 7,160,300 B2 | 1/2007 | Jackson |
| 7,179,261 B2 | 2/2007 | Sicvol et al. |
| 7,250,052 B2 | 7/2007 | Landry et al. |
| 7,465,306 B2 | 12/2008 | Pond, Jr. et al. |
| 7,470,279 B2 | 12/2008 | Jackson |
| 7,476,240 B2 * | 1/2009 | Raymond .......... A61B 17/7002 606/279 |
| 7,491,218 B2 | 2/2009 | Landry et al. |
| 7,520,879 B2 | 4/2009 | Justis et al. |
| 7,547,318 B2 | 6/2009 | Birkmeyer et al. |
| 7,563,264 B2 | 7/2009 | Landry et al. |
| 7,572,281 B2 | 8/2009 | Runco et al. |
| 7,691,132 B2 | 4/2010 | Landry et al. |
| 7,758,617 B2 | 7/2010 | Iott et al. |
| 7,909,856 B2 | 3/2011 | Yuan et al. |
| 7,914,558 B2 | 3/2011 | Landry et al. |
| 8,038,699 B2 | 10/2011 | Cohen et al. |
| 8,246,624 B2 | 8/2012 | Forton et al. |
| 2003/0125742 A1 | 7/2003 | Yuan et al. |
| 2003/0208203 A1 * | 11/2003 | Lim .................. A61B 17/7083 606/86 A |
| 2005/0085813 A1 | 4/2005 | Spitler et al. |
| 2005/0131419 A1 * | 6/2005 | McCord ............ A61B 17/7085 606/99 |
| 2005/0131422 A1 | 6/2005 | Anderson et al. |
| 2005/0215999 A1 | 9/2005 | Birkmeyer et al. |
| 2005/0277934 A1 | 12/2005 | Vardiman |
| 2006/0074418 A1 | 4/2006 | Jackson |
| 2006/0095035 A1 | 5/2006 | Jones et al. |
| 2006/0111712 A1 | 5/2006 | Jackson |
| 2006/0111713 A1 | 5/2006 | Jackson |
| 2006/0142761 A1 | 6/2006 | Landry et al. |
| 2006/0241600 A1 | 10/2006 | Ensign et al. |
| 2006/0247630 A1 | 11/2006 | Iott et al. |
| 2006/0247636 A1 | 11/2006 | Yuan et al. |
| 2006/0293680 A1 | 12/2006 | Jackson |
| 2007/0078460 A1 | 4/2007 | Frigg et al. |
| 2007/0173831 A1 | 7/2007 | Abdou |
| 2007/0213714 A1 | 9/2007 | Justis |
| 2007/0233097 A1 | 10/2007 | Anderson et al. |
| 2008/0009864 A1 | 1/2008 | Forton et al. |
| 2008/0039838 A1 | 2/2008 | Landry et al. |
| 2008/0045956 A1 | 2/2008 | Songer |
| 2008/0045957 A1 | 2/2008 | Landry et al. |
| 2008/0077138 A1 * | 3/2008 | Cohen .................. A61B 17/708 606/86 A |
| 2008/0082103 A1 * | 4/2008 | Hutton ............... A61B 17/0218 606/272 |
| 2008/0119849 A1 * | 5/2008 | Beardsley .......... A61B 17/7032 606/306 |
| 2008/0125788 A1 | 5/2008 | Cohen et al. |
| 2008/0154279 A1 | 6/2008 | Schumacher |
| 2008/0154280 A1 | 6/2008 | Schumacher et al. |
| 2008/0161857 A1 | 7/2008 | Hestad et al. |
| 2008/0183215 A1 | 7/2008 | Altarac et al. |
| 2008/0269805 A1 | 10/2008 | Dekutoski et al. |
| 2008/0288005 A1 | 11/2008 | Jackson |
| 2008/0312703 A1 * | 12/2008 | Hestad ............... A61B 17/7085 606/86 A |
| 2009/0012563 A1 | 1/2009 | Alleyne et al. |
| 2009/0082811 A1 | 3/2009 | Stad et al. |
| 2009/0105774 A1 * | 4/2009 | Jones .................. A61B 17/7083 606/86 A |
| 2009/0143828 A1 | 6/2009 | Stad et al. |
| 2009/0171391 A1 * | 7/2009 | Hutton ............... A61B 17/7032 606/246 |
| 2010/0249856 A1 | 9/2010 | Iott et al. |
| 2011/0093014 A1 | 4/2011 | Davis et al. |
| 2013/0190825 A1 * | 7/2013 | Perrow .............. A61B 17/8042 606/281 |

* cited by examiner

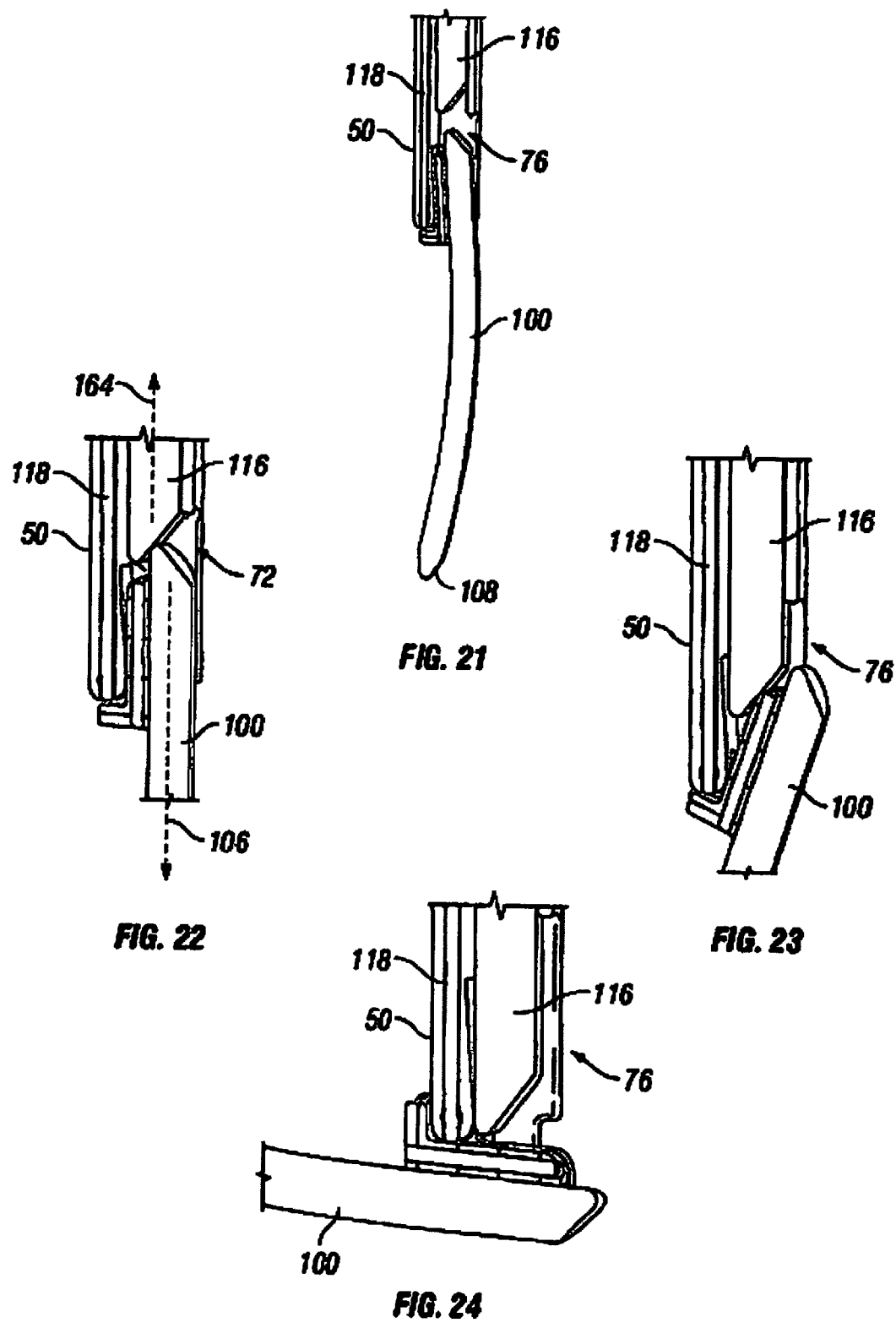

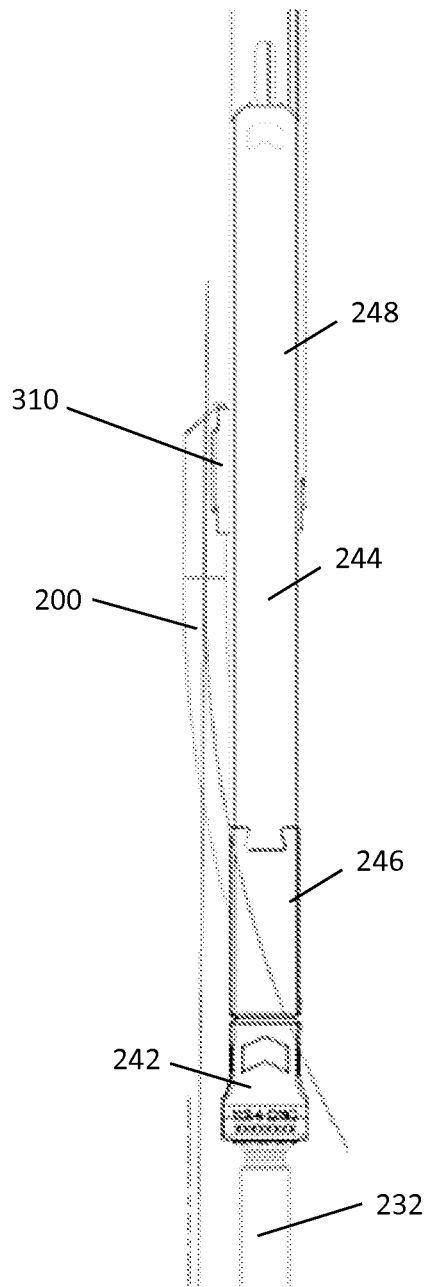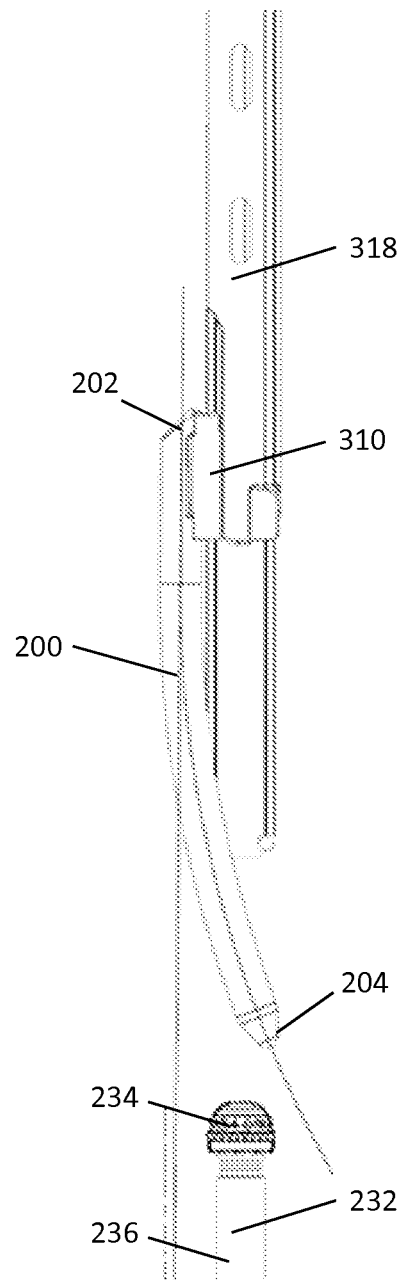
*FIG. 29A*    *FIG. 29B*

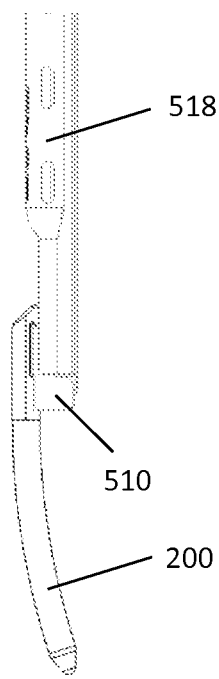 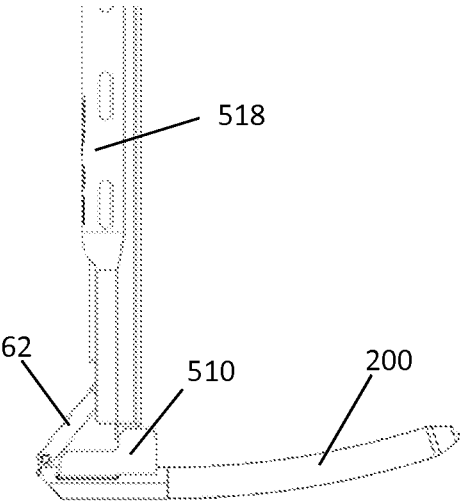
FIG. 37E          FIG. 37F
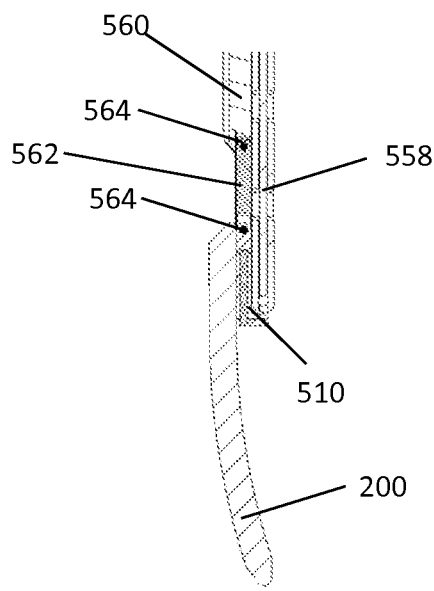 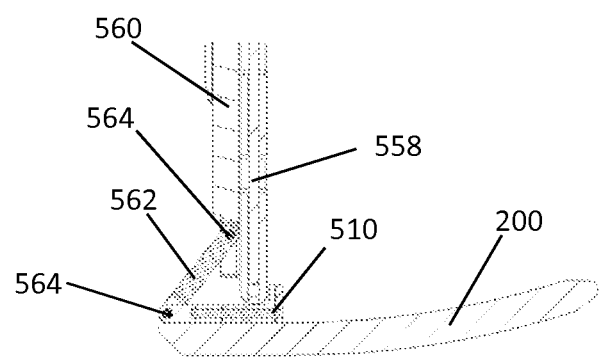
FIG. 37G          FIG. 37H

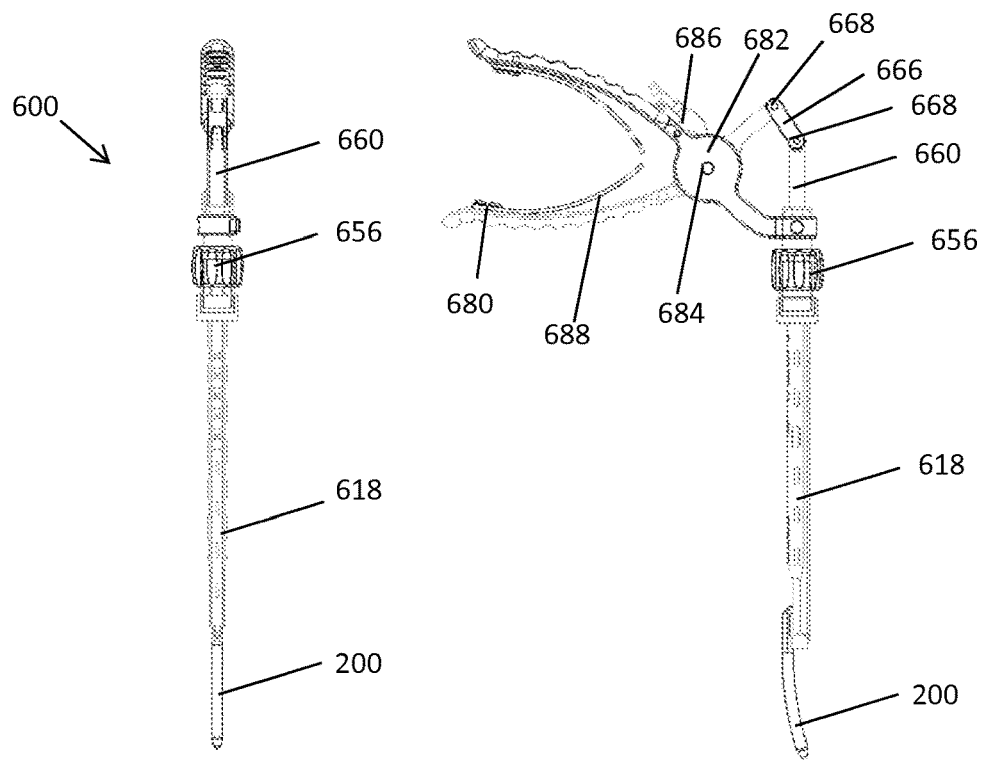
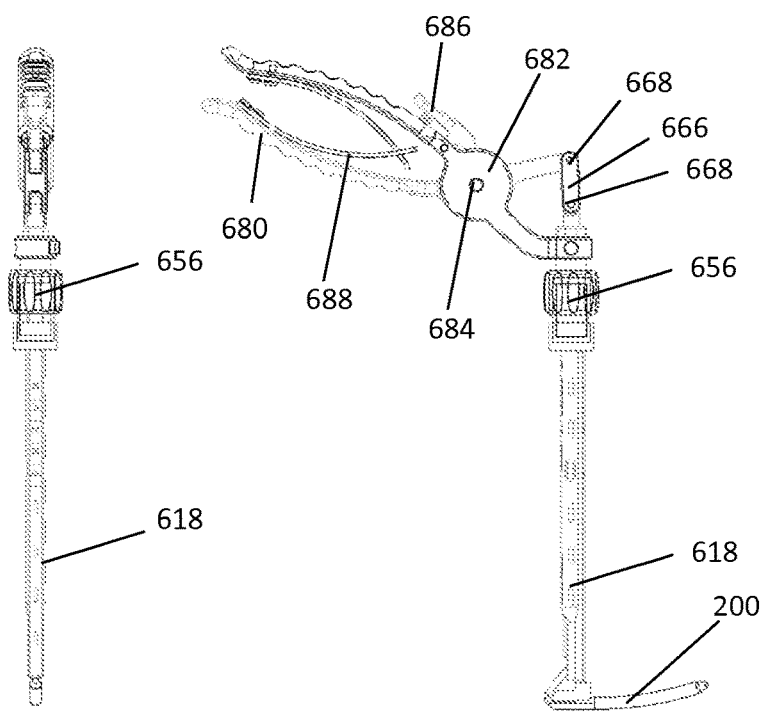
*FIG. 38B*  *FIG. 38C*
*FIG. 38D*  *FIG. 38E*

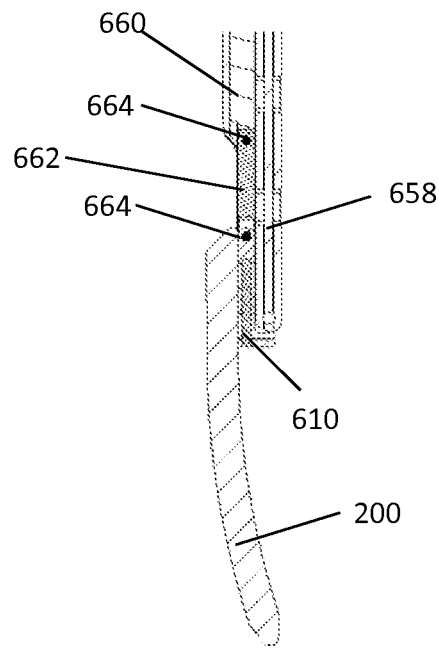
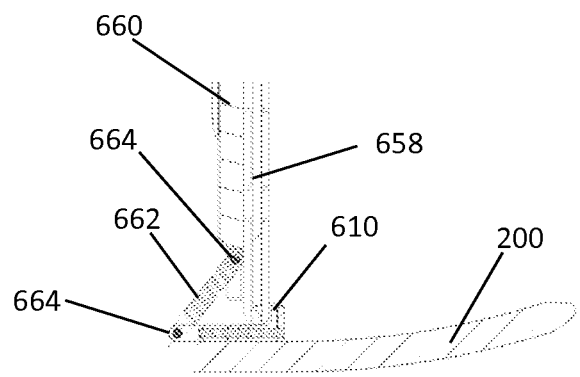
FIG. 38F    FIG. 38G
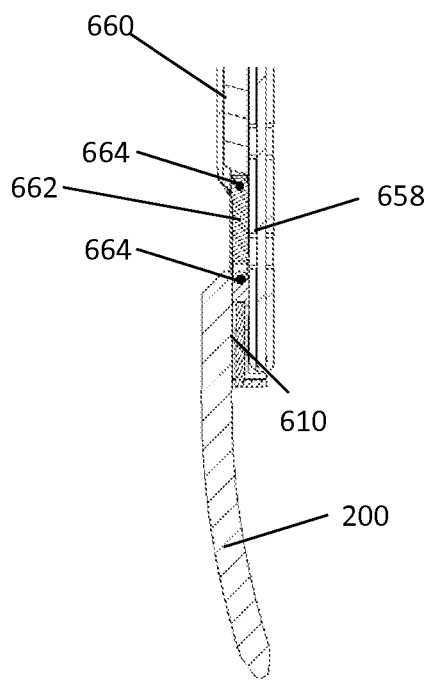
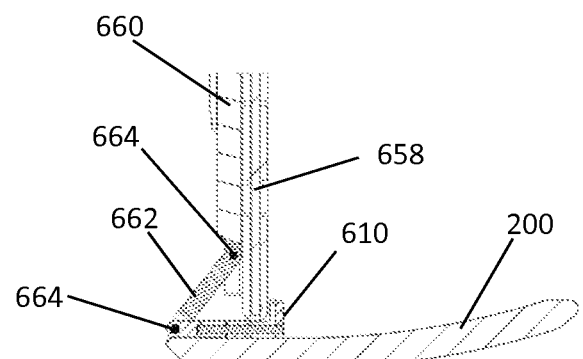
FIG. 38H    FIG. 38I

DEVICES AND METHODS FOR INSERTING A VERTEBRAL FIXATION MEMBER

CROSS REFERENCE TO RELATED APPLICATION

The present application is a continuation of U.S. patent application Ser. No. 14/516,631 filed on Oct. 17, 2014, which is a continuation-in-part of U.S. patent application Ser. No. 12/413,058 filed on Mar. 27, 2009, now U.S. Pat. No. 8,900,238, the entire disclosure of which is incorporated herein by reference in its entirety for all purposes.

FIELD OF THE INVENTION

The present invention relates generally to devices and methods for inserting a vertebral fixation member, and more particularly, but not exclusively, to rod insertion devices and methods.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member can help restore spinal elements to a pain free situation, or at least may help reduce pain or prevent further injury to the spine.

As the science and technology of spine surgery continues to progress, there is an increasing interest in developing alternative, minimally invasive, methods to conventional "open" spine surgery. The goals of these less invasive alternatives are to avoid the surgical exposure, dissection, and retraction of muscles and tissues that is necessary with "open" surgery. In general, a minimally invasive spine surgery system should be able to perform the same procedure as the traditional open technique, but through smaller incisions instead of one longer incision. As a result, some physicians feel that using a minimally invasive spine surgery system generally causes less soft tissue damage, reduces blood loss and reduces recovery time. In addition, patients generally prefer the smaller scars that are left using a minimally invasive approach.

Historically, spine fusion surgery including pedicle screw fixation with deep placement of rods has been one area that has presented significant challenges for minimally invasive approaches. However, advancement in technologies such as fluoroscopy and improvements in optics have contributed to the advent of a few minimally invasive spine fusion surgery techniques.

SUMMARY OF THE INVENTION

Devices, systems, and methods for inserting a vertebral stabilization member are disclosed. The vertebral stabilization system may include an elongate stabilization member, such as a rod, positioned between one or more anchors, such as pedicle screws with tulip heads. After the pedicle screws have been implanted, the rod may be inserted, reduced, and/or locked into the tulip head. The rods may be inserted for example using an insertion device, which may be used to introduce the rod to the surgical site using, for example, an open, mini-open, percutaneous or minimally-invasive method. For minimally invasive surgical procedures, for example, there may be limited access locations for the rods. For example, if a sleeve is used during the procedure, the rod may be placed through or proximate to the sleeve. In the alternative, one or more extension tabs may be connected to the anchor, and the rod may be placed through or proximate to the extension tabs. The position of the insertion device and the rod preferably eases rod insertion while limiting skin, muscle, and tissue damage.

In addition, many existing rod holders are fixed position with limited freedom of movement, which increases the potential for non-ideal rod placement. This may result in additional or elongated incisions, excessive rod reduction, or complete removal of the rod and reinsertion increasing muscle and tissue damage. Accordingly, an articulating design for the insertion device may be provided allowing for articulating motion between an initial, insertion orientation and a final, installed orientation. This articulating motion results in more controlled and consistent rod insertion and a reduction in muscle and tissue damage, for example, in one-to-two level fusion cases. The insertion device can maintain and control the rod position without requiring any additional incisions.

According to an embodiment, an insertion device is suitable for installing an elongate stabilization member in a first orientation and pivoting the elongate stabilization member to a second orientation, for example, angled at about 90° relative to the first orientation. The insertion device includes an outer guide tube, a pin assembly, and a pusher member. The outer guide tube has an elongate body extending from a first end to a second end and has a central longitudinal opening extending therethrough. The pin assembly includes a pin extending through the central longitudinal opening of the outer guide tube. The pin has a first end engaged with a thumb wheel and a second end configured to engage a clamping element, such that when the thumb wheel is rotated, the pin linearly moves and engages a portion of the clamping element. The pin assembly may be configured to enable locking and unlocking of the elongate stabilization member to the insertion device. The pusher member extends through the central longitudinal opening of the outer guide tube having a first end connected to a handle and a second end connected to the clamping element, such that when the handle is depressed, the pusher member linearly moves to cause the elongate stabilization member to pivot.

The insertion device may have one or more of the following features, for example: a first handle connected to the pusher member by a first linking element and a second handle connected to the outer guide tube; the first and second handles connected together by a ratchet in the shape of a wheel having a plurality of teeth positioned around the periphery of the wheel; the first and second handles locked in position relative to one another by depressing a locking member having teeth corresponding to and designed to engage the ratchet; and the pusher member connected to the clamping element with a second linking element configured to pivot in response to linear motion of the pusher member.

According to one embodiment, a minimally invasive vertebral stabilization system includes a first anchor, an elongate stabilization member, and a stabilization member insertion device. The first anchor is deliverable to a vertebral body of a patient through a first opening with at least one extended tab connected thereto. The at least one extended tab defines an open central portion and a central longitudinal axis. The elongate stabilization member extends from a proximal end to a distal end.

The stabilization member insertion device releasably and rotatably links to the elongate stabilization member. The stabilization member insertion device is configured and dimensioned to be received within the open central portion such that the insertion device is moveable along the central longitudinal axis. The elongate stabilization member may be cantilevered off the stabilization member insertion device such that at least a portion of the elongate stabilization member is positioned outside the at least one extended tab. This configuration may allow for longer rods to be utilized.

The elongate stabilization member is deliverable in a first orientation substantially parallel to the central longitudinal axis of the open central portion; and, independent of movement along the central longitudinal axis, the elongate stabilization member is rotatably actuatable by the stabilization member insertion device to extend in a second orientation angled with respect to the first orientation to position the stabilization member in relation to the first anchor. The insertion and articulation of the elongate stabilization member may be controlled with the use of fluoroscopy, for example, to help guide axial and rotation movements.

In alternative to providing an instrument-sleeve or separate sleeve, the anchor may be connected to one or more extended tabs. The extended tabs may extend upwardly from an upper portion of the anchor. The extended tabs may have an elongate curved body, for example, to mimic a sleeve. The extended tabs may include a pair of diametrically opposed extended tabs defining opposed longitudinal openings. The longitudinal openings may provide lateral access to and from the open central portion. For example, a portion of the elongate stabilization member may be extendable through the longitudinal openings. The extended tab may be a multi-part component. For example, the extended tab may include a first extension element connected to the first anchor at a break point and a second extension element connected to the first extension element. The second extension element may be connected to the first extension element via a dovetail and/or welded connection, for example.

Instead of positioning the elongate stabilization member through the open central portion, the elongate stabilization member may be cantilevered off the stabilization member insertion device. In particular, at least a portion of the elongate stabilization member is not positioned within the open central portion and is positioned outside the at least one extended tab. For example, the proximal end of the elongate stabilization member may not be contained within the open central portion in the first orientation.

The minimally invasive vertebral stabilization system may include a second anchor deliverable to a vertebral body of a patient through a second opening with one or more extended tabs connected to the second anchor. The extended tabs connected the second anchor may be the same or similar to the extended tabs connected to the first anchor. The first and second anchors may include a bone fastener, such as polyaxial screws, bone screws, hooks, etc. with a coupling element attached thereto. The coupling element, such as a tulip element, yoke, or the like, may be provided for coupling the elongate stabilization member to the bone fastener. Clamp and/or wedge elements may be used to secure the bone fastener in the coupling element. A locking cap may be used to secure the rod in the coupling element. The rod should be seated firmly in the coupling element in order for the elements of the fixation device to be secured. The stabilization member insertion device may be operable to place the stabilization member between the first and second anchors.

The elongate stabilization member may be in the form of a rod. The rod may have a substantially straight shape or a curvilinear shape. The rod may have at least one indentation along its length, for example, such that the stabilization member insertion device may clampably link to the stabilization member about the indentation(s). The proximal end of the rod may be configured and dimensioned to interact with the stabilization member insertion device. The proximal end of the rod may be angled with respect to a longitudinal axis of the rod, and the proximal end may define a concave surface.

The elongate stabilization member may be releasably clampable to the insertion device between first and second clamping members at a clamping location spaced from a midline of the elongate stabilization member. The first clamping member may include a first generally cylindrical protrusion insertable into a distal portion of the insertion device and the second clamping member may include a second generally cylindrical protrusion insertable into the distal portion of the insertion device. The first and second clamping members may be coupled by a pin extending through a first and second opening in the first and second clamping members, respectively.

According to another embodiment, a minimally invasive vertebral stabilization system includes an anchor, an elongate stabilization member, and a stabilization member insertion device. The anchor is deliverable to a vertebral body of a patient with one or more extended tabs connected thereto. The extended tab includes a first extension element connected to the first anchor at a break point and a second extension element connected to the first extension element. The extended tab defines an open central portion and a central longitudinal axis. The elongate stabilization member extends from a proximal end to a distal end.

The stabilization member insertion device releasably and rotatably links to the proximal end of the elongate stabilization member. The stabilization member insertion device is configured and dimensioned to be received within the open central portion such that the insertion device is moveable along the central longitudinal axis. The elongate stabilization member is cantilevered off the stabilization member insertion device such that at least a portion of the elongate stabilization member is positioned outside the second extension element of the at least one extended tab.

The elongate stabilization member is deliverable in a first orientation substantially parallel to the central longitudinal axis of the open central portion; and, independent of movement along the central longitudinal axis, the elongate stabilization member is rotatably actuatable by the stabilization member insertion device to extend in a second orientation angled with respect to the first orientation to position the stabilization member proximate to the anchor. The second orientation may be angled at about 90° relative to the first orientation.

According to another embodiment, a minimally invasive vertebral stabilization system includes an anchor, an elongate stabilization member, and a stabilization member insertion device. The anchor is deliverable to a vertebral body of a patient with one or more extended tabs connected thereto. The extended tab defines an open central portion and a central longitudinal axis. The extended tabs include a pair of diametrically opposed extended tabs defining opposed longitudinal openings. The longitudinal openings provide lateral access to the open central portion. The elongate stabilization member extends from a proximal end to a distal end. The stabilization member insertion device releasably and rotatably links to the proximal end of the elongate stabilization member. The stabilization member insertion device is configured and dimensioned to be received within the open central portion such that the insertion device is moveable along the central longitudinal axis. The elongate stabilization member is cantilevered off the stabilization member insertion device such that at least a portion of the elongate stabilization member is positioned outside of one of the longitudinal openings. The elongate stabilization member is deliverable in a first orientation substantially parallel to the central longitudinal axis of the open central portion; and, independent of movement along the central longitudinal axis, the elongate stabilization member is rotatably actuatable by the stabilization member insertion device to extend in a second orientation angled with respect to the first orientation to position the stabilization member proximate to the anchor.

BRIEF DESCRIPTION OF THE DRAWINGS

The invention will be more readily understood with reference to the embodiments thereof illustrated in the attached drawing figures, in which:

FIG. 21 is a partial cross-sectional view of the insertion device of FIG. 2 shown in a first position;

FIGS. 22-24 are partial cross-sectional views of the insertion device of FIG. 2 shown in second, third and fourth positions, respectively;

FIGS. 29A and 29B are close-up side views of the insertion apparatus shown in FIG. 27 with (FIG. 29A) and without (FIG. 29B) an extended tab and tulip present;

FIGS. 37A-37H depict alternative view of an insertion apparatus according to another embodiment, which may be suitable for use in an open or mini-open procedure; and FIGS. 38A-38I depict alternative views of an insertion apparatus according to yet another embodiment.

Throughout the drawing figures, it should be understood that like numerals refer to like features and structures.

DETAILED DESCRIPTION

The various embodiments of the invention will now be described with reference to the attached drawing figures. The following detailed description of the invention is not intended to be illustrative of all embodiments. In describing the various embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose. The features of one embodiment may be employed with other embodiments as the skilled artisan would recognize, even if not explicitly stated herein.

Figure 1:
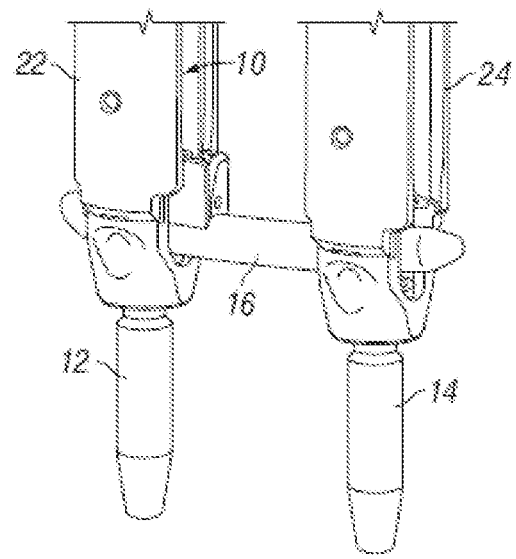
FIG. 1 is a perspective view of one embodiment of a stabilization member and insertion device shown during on embodiment of an installation method according to the present invention.
Figure 2:
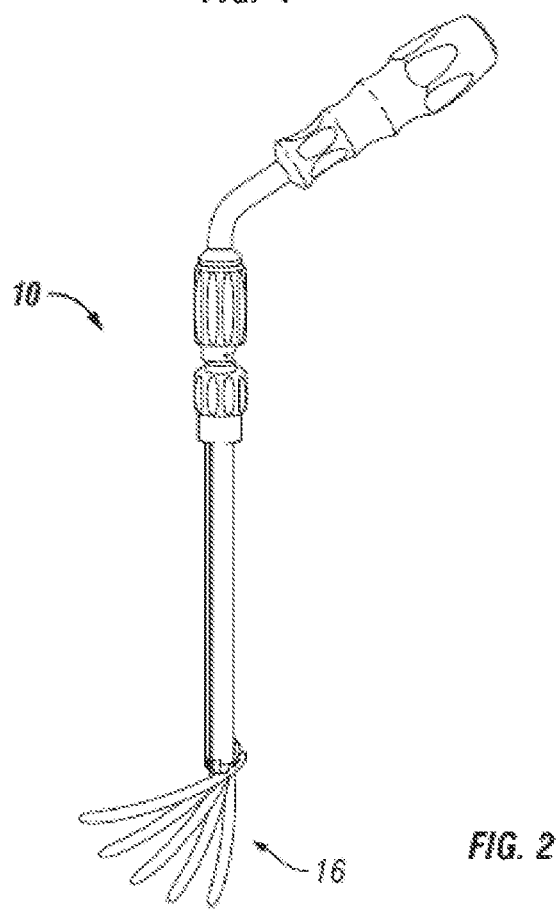
FIG. 2 is a perspective view of one embodiment of a stabilization member insertion device according to the present invention.

Referring to FIG. 1, one embodiment of a stabilization member insertion device 10 is shown positioned within one embodiment of a sleeve 22 that is mated to a first anchor 12. A second anchor 14 is shown attached to a second sleeve 24. A connecting member or stabilization member 16 is shown attached to device 10 and is configured to connect and/or extend between the first and second anchors 12, 14 for stabilizing at least a portion of a vertebrae of a patient. According to one variation, first anchor 12 may be positioned within a body of a patient through any known surgical methods, including but not limited to, through a first minimally invasive or percutaneous opening. Second anchor 14 is also positionable within a body of a patient through any known surgical methods, including but not limited to, through a second minimally invasive or percutaneous opening. In the alternative, first and second anchors 12, 14 may be inserted through an open, mini-open, or mixed open and minimally invasive procedure. In one embodiment, first and second anchors 12, 14 are configured to engage first and second vertebra.

Stabilization member 16 is positionable within the body of a patient through a first opening in the skin to engage and connect first and second anchors 12, 14. According to one embodiment, one of sleeves 22, 24 may extend from anchors 12, 14 and facilitate insertion of anchors 12, 14 into a vertebral body. Stabilization member 16 may be installed between anchors 12, 14 and clamping members, screw caps or set screws may be installed for fixation of stabilization member 16 to anchors 12, 14. Stabilization member 16 may be installed through any known surgical methods including, but not limited to minimally invasively, percutaneously or through an open procedure or non-percutaneously into receiving portions or channels 26 of anchors 12, 14. According to one embodiment, connecting member or stabilization member 16 generally comprises an elongate rod or shaft. Stabilization member 16 may have an arcuate or curvilinear shape. In alternative embodiments, however, stabilization member 16 can include any configuration known for a rod, implant, or fastener, and can be straight or have any curvature along its length including a compound curvature. As shown in FIG. 1, a stabilization member insertion device 10 may be inserted into sleeve 22 to facilitate insertion of stabilization member 16 into anchors 12, 14. Although a second sleeve 24 is depicted in FIG. 1 as being attached to anchor 14, a second sleeve 24 may or may not be connected to second anchor 14, depending on the preference of a surgeon user.

In one embodiment, stabilization member insertion device 10 is releasably and rotatably linked to the stabilization member 16 and the stabilization member insertion device 10 is configured and dimensioned to be received within a single sleeve 22, 24 such that the insertion device 10 and stabilization member 16 are moveable in the longitudinal direction within the sleeve to position stabilization member 16 adjacent the distal end thereof. As will be discussed in more detail below, stabilization member 16 is deliverable through the sleeve in a first orientation substantially parallel to the axis of the sleeve and is rotatable to a second orientation at an angle with respect to the first orientation. Furthermore, the stabilization member 16 is rotatably actuatable by insertion device 10 independent of movement along the axis of the sleeve, i.e. the stabilization member 16 may be rotated by insertion device 10 anywhere along the length of the sleeve. Such a feature may be particularly advantageous, for example, to adjust the pathway or route that the stabilization member 16 travels through the body tissue during installation. In this regard, those skilled in the art will appreciate that a virtually limitless number of different pathways that a stabilization member 16 may travel and this features provides great flexibility to a surgeon user. In addition, due to the independent aspect of the rotation of the stabilization member, rotation may be actuated or independently controlled without moving the insertion device with respect to sleeve 22. In this regard, rotation of stabilization member 16 may be rotated without downward exertion of force upon the sleeve and/or anchor.

Figure 3:
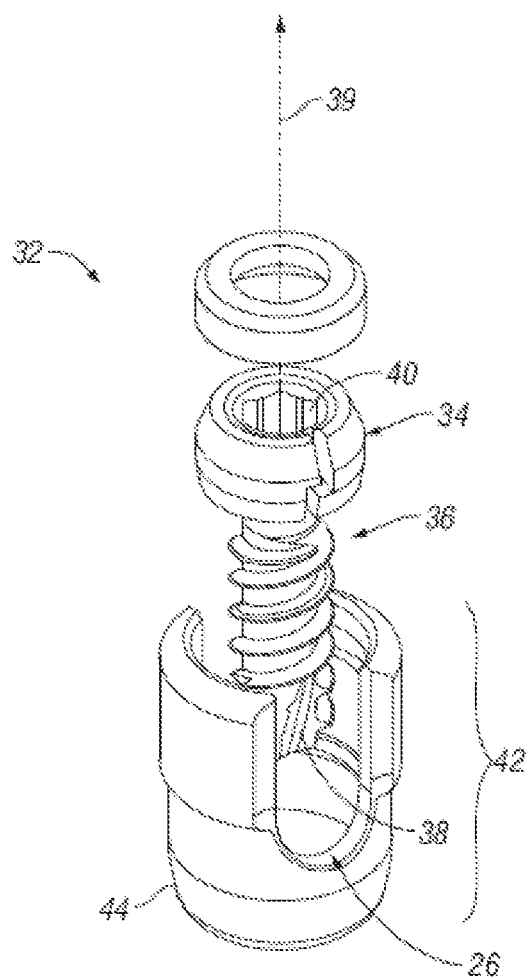
FIG. 3 is an exploded view of one embodiment of a screw.
Figure 4:
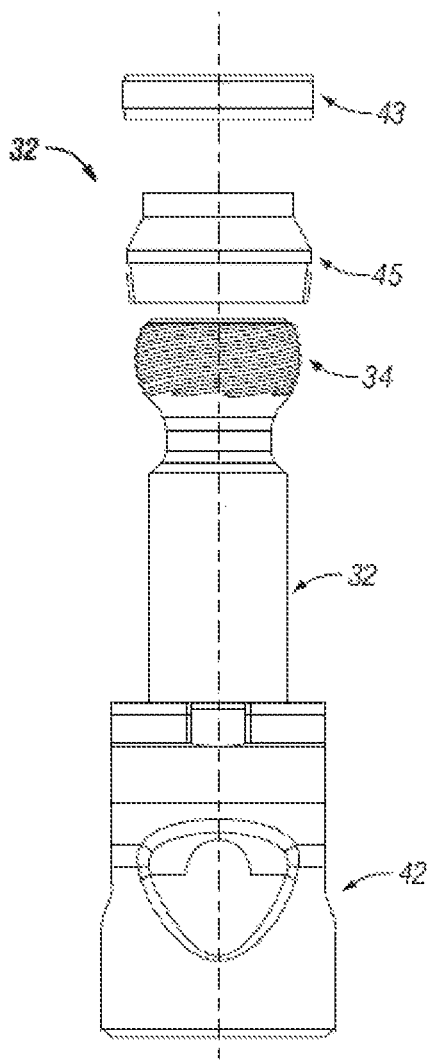
FIG. 4 is an exploded view of another embodiment of a screw.
Figure 5:
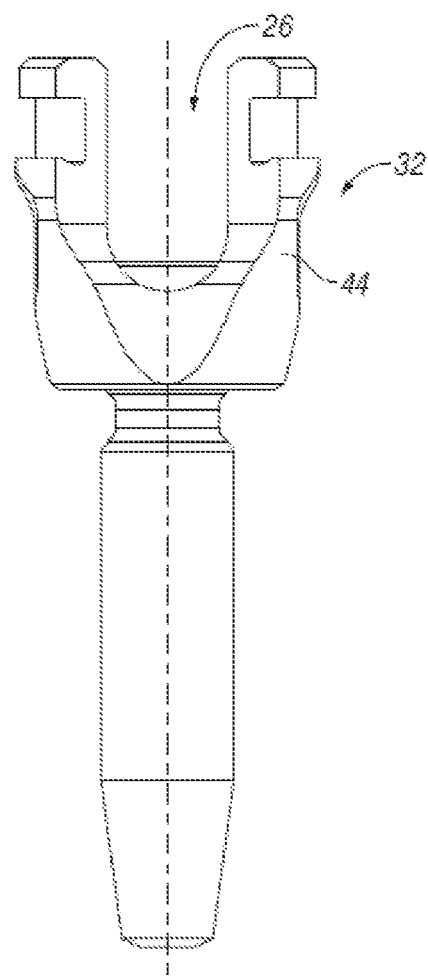
FIG. 5 is an assembly view of the embodiment of the screw of FIG. 4.

Referring now to FIGS. 3-5, exemplary embodiments of anchors that may be utilized with the invention are shown. Referring to FIG. 3, one embodiment of an anchor 32 is shown and generally comprises a bone fastener such as a bone screw 32 with a head 34 and a shaft or shank 36 having bone engaging threads. As shown in FIG. 3, screw 32 is cannulated with a central passage or lumen 38 extending along a central axis 39, however, non-cannulated screws may also be used. Head 34 includes a tool engagement surface or opening 40 configured to receive a driving tool to provide torque and drive the screw into bone. In one embodiment, screw 32 is a polyaxial screw assembly that has a coupling element 42 pivotably coupled to, head 34 of screw 32. A wedge 43 and clamp assembly 45 may be housed within coupling element 42 to facilitate locking the screw 32 with respect to coupling element 42. In this regard, screw 32 is capable of rotating within coupling element 42 to selectably assume a plurality of angles. Referring to FIGS. 4-5, another exemplary embodiment of a bone screw 32 is shown. Still another example of a polyaxial screw that may be used with the present invention is described in U.S. Pat. No. 7,503,924, the entire contents of which are incorporated by reference.

Referring to the embodiments of FIGS. 3-5, coupling element 42 is configured and adapted to receive the stabilization member 16. In general, coupling element 42 includes a U-shaped body 44 defining a channel 26 in which stabilization member 16 may be locked or fixed in place by, for example, a locking cap. In alternate embodiments, alternative means of rigidly coupling stabilization member 16 to an anchor may be used by those skilled in the art, including alternative configurations of coupling elements and locking devices or methods. In one embodiment, coupling element 42 includes features to couple with sleeves 22, 24.

Figures 6, 7:
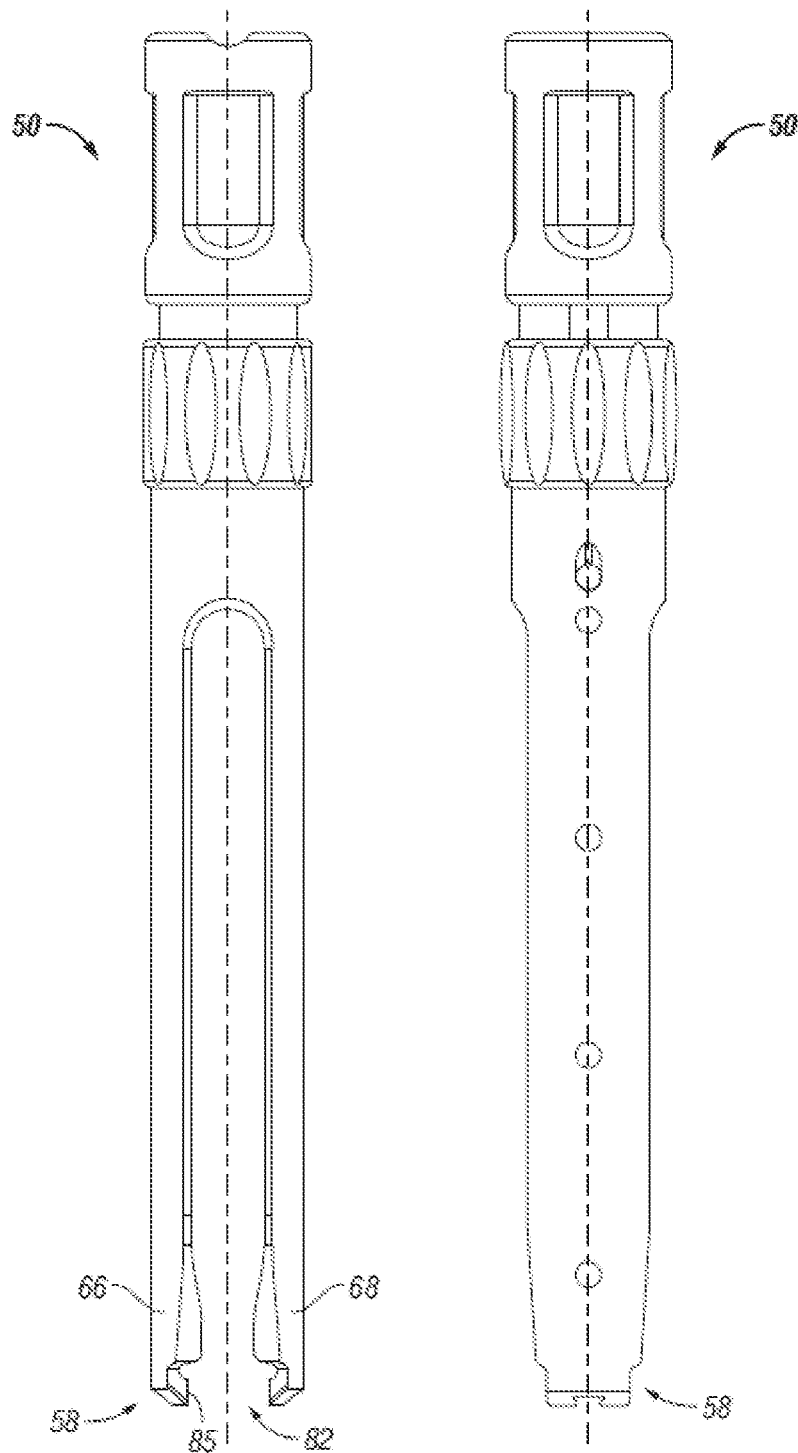
FIGS. 6-7 are side and front views of one embodiment of an access sleeve.

In the illustrated embodiment, a sleeve may extend from the anchors 12, 14 and provide a portal or passageway through the body of a patient to access anchors 12, 14. Referring to FIGS. 6-7, one embodiment of a sleeve 50 according to the invention is shown comprising cannula 54 extending from a proximal end 56 to a distal end 58 along an axis 60. A central channel 62 extends axially through sleeve 50. In this regard, cannula 54 generally comprises an extended tube with a generally cylindrical top portion 64 and a pair of generally rigid arms 66, 68 extending axially from top portion 64 in a distal direction. Slots or openings 76 extend along the lateral sides of sleeve 50 to provide access to central channel 62 of sleeve 50. Sleeve 50 may be made of any material suitable for surgical instruments. In one preferred embodiment, sleeve 50 may be made of a metallic material.

In operation, arms 66, 68 of sleeve 50 may include a retainer portion 82 at its distal end to attach an anchor to the distal end of sleeve 50. In this regard, arms 66, 68 may include projections 84 extending laterally inward from the distal end to engage a corresponding feature on the anchor to provide additional retention capability.

When sleeve 50 is assembled to an anchor, as shown in FIG. 1, coupling element 42 of bone screw 32 is received within retainer portion 82 at a distal end 58 of sleeve 50. In this regard, retainer portion 82 may snappably or resiliently receive the coupling element 42 of screw 32. The inner wall 85 of retainer portion 82 is shaped to conform to the outer perimeter of coupling element 42 such that when arms 66, 68 engage an anchor, the coupling element 42 of screw 32 is rotationally and axially fixed with respect to sleeve 50 or radially contained within sleeve 50

Figure 8:
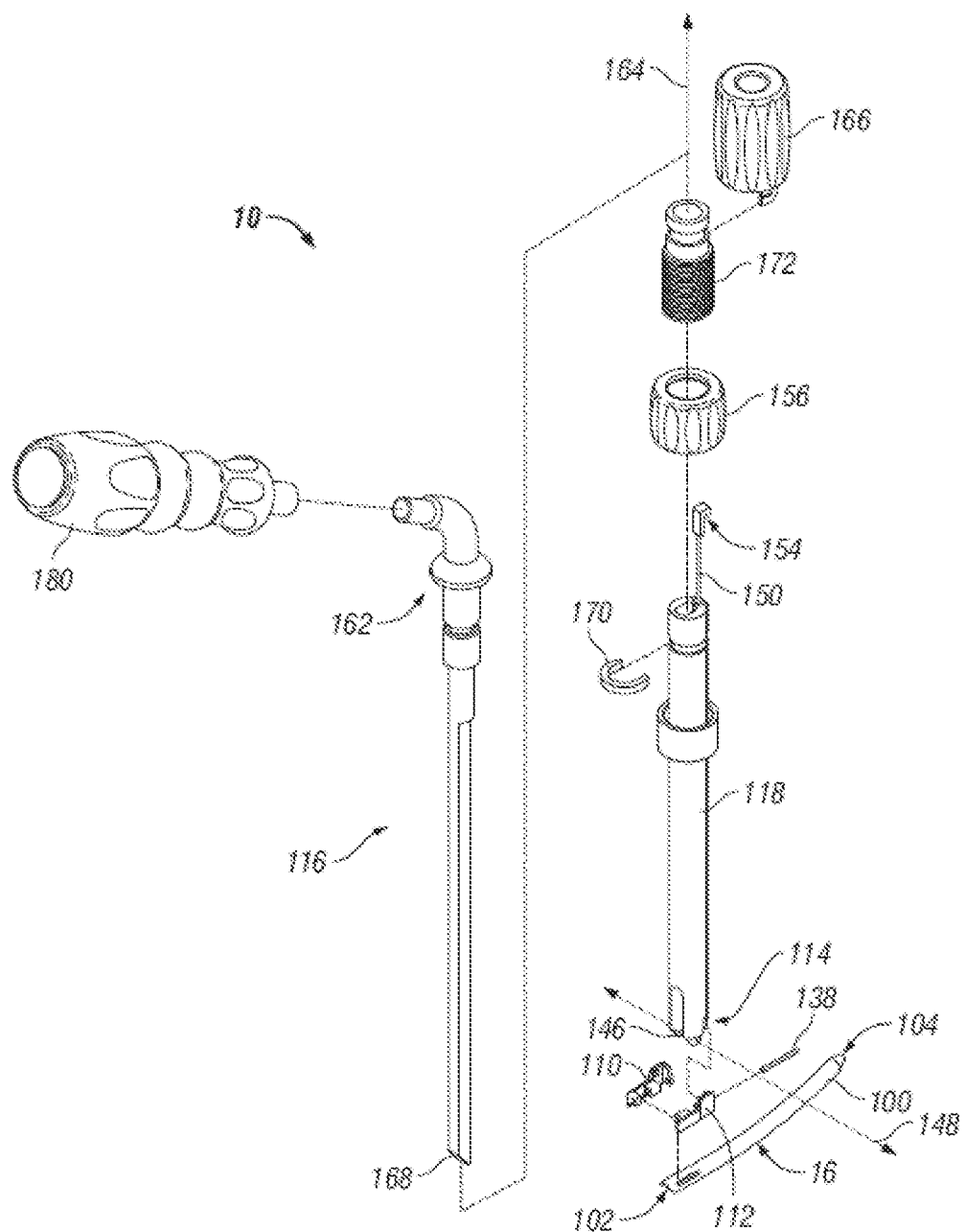
FIG. 8 is an exploded view of one embodiment of the insertion device of FIG. 2.
Figure 9:
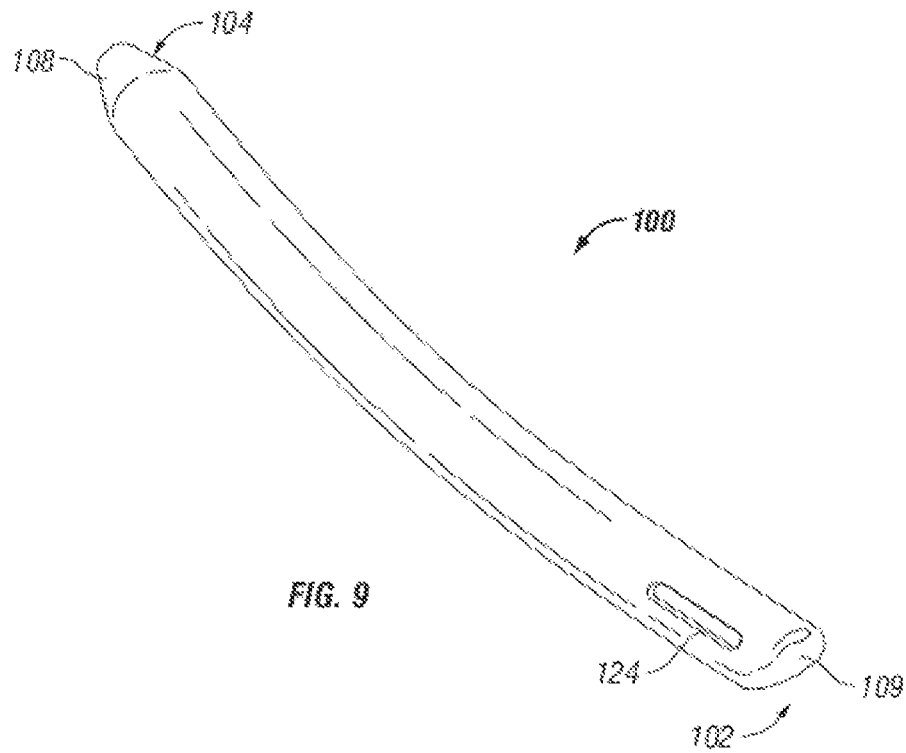
FIG. 9 is a perspective view of one embodiment of a stabilization member according to the present invention.
Figure 10:
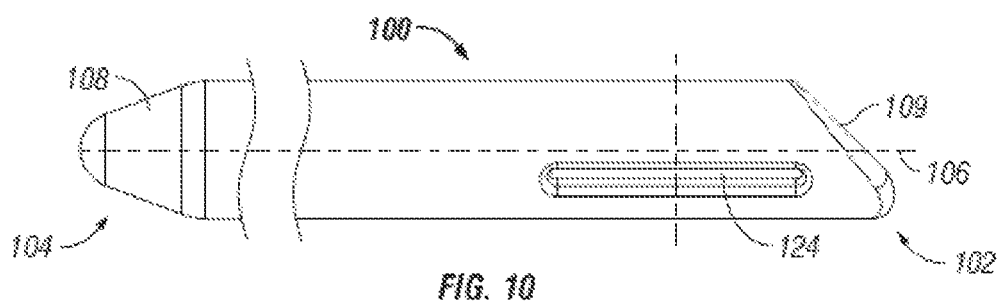
FIGS. 10-11 are enlarged side and top views of the stabilization member of FIG. 9.
Figure 11:
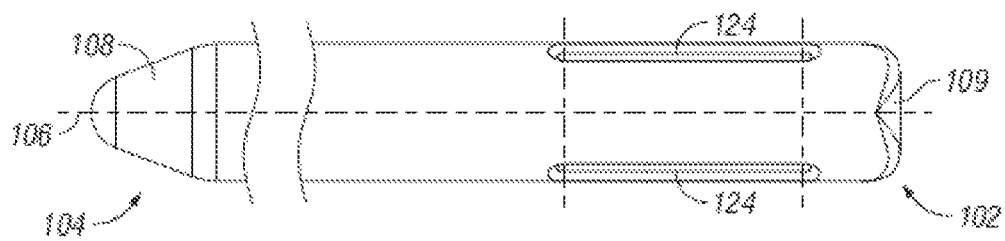

Referring now to FIGS. 8-11, one embodiment of a stabilization member 16 and insertion device 10 is shown. As shown in FIGS. 9-11, stabilization member 16 generally comprises an elongate rod 100 extending from a proximal end 102 to a distal end 104 along an axis 106. In one embodiment, rod 100 is curved or arcuate along its length. However, in alternate embodiments, rod 100 may have any alternate shape. According to one aspect of the embodiment, rod 100 includes a generally tapered or conical shaped nose or tip 108 at its distal end 104 to facilitate insertion and installation of rod 100 into the body of a patient. In alternate embodiments, tip 108 may have varied shapes and sizes. Proximal end 102 of rod 100 comprises a generally concave or rounded ramped tip surface 109 angled with respect to longitudinal axis 106 configured and dimensioned to interface or engage with actuating or pushing member 116 of insertion device 10.

Referring to FIG. 8, insertion device 10 generally comprises a means for clamping to or holding stabilization member 16 and means for controllably actuating or rotating the stabilization member 16 about the distal end of the device. According to one variation, insertion device 10 is an assembly generally comprising a pair of clamp members 110, 112 pivotably attached adjacent a distal end 114 that may be selectably actuatable to clamp, fix or hold the stabilization member 16 adjacent the distal end thereof. Insertion device 10 additionally comprises a drive shaft or actuatable pusher assembly 116 extendable centrally within an outer guide tube 118 and linearly advanceable with respect thereto to facilitate the rotation or pivoting of the stabilization member 16 with respect to guide tube 118.

Referring again to FIGS. 9-11, in one embodiment, rod 100 may include a pair of diametrically opposed indentations 124 spaced from proximal end 102 of rod 100. In one variation, indentations 124 are generally elongate grooves extending generally parallel with axis 106. Indentations 124 are configured and dimensioned to releasably rotatably engage clamp members 110, 112 of insertion device 10 such that rod 100 may pivot with respect to distal end 114. To attach rod 100 to clamp members 110, 112, clamp members may be separatable to engage or snap into indentations 124. In operation, once ridges cooperatively engage indentations 124, rod 100 may rotate or pivot about distal end 114.

One embodiment of a means for clamping comprises a left clamp member 110 and a right clamp member 112 pivotably attached to a distal end of guide tube 118. A pair of openings 146 are provided adjacent the distal end of guide tube 118 and receives clamp members 110, 112 therein to releasably clamp to rod 100 such that rod 100 may rotate thereabout.

Figure 12:
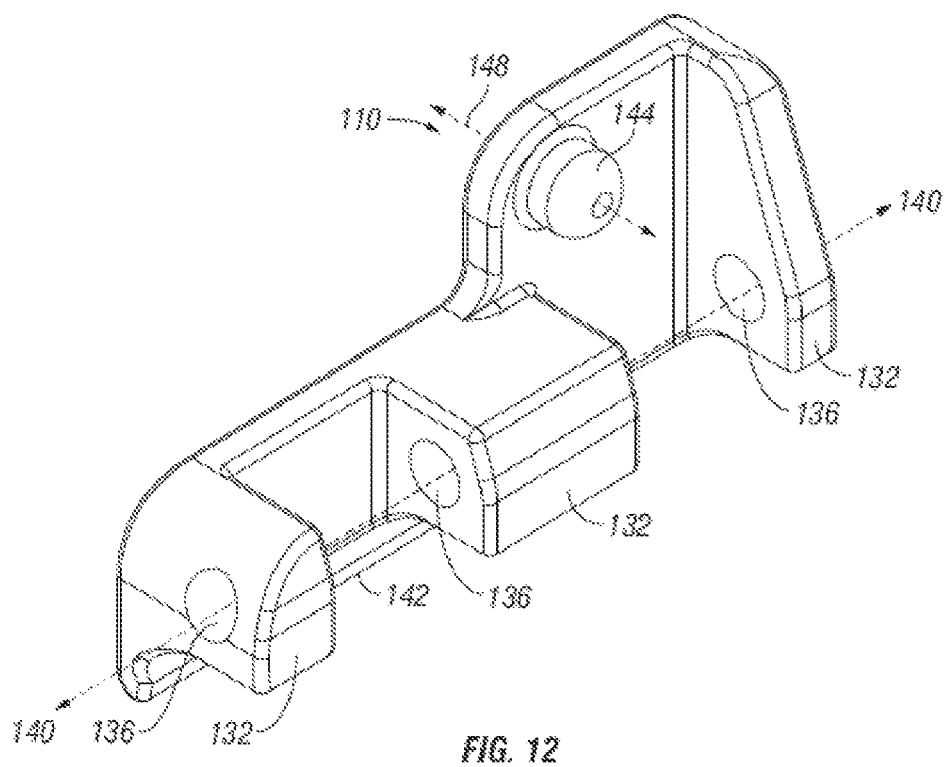
FIGS. 12-13 are perspective views of left and right clamp members, respectively.
Figure 13:
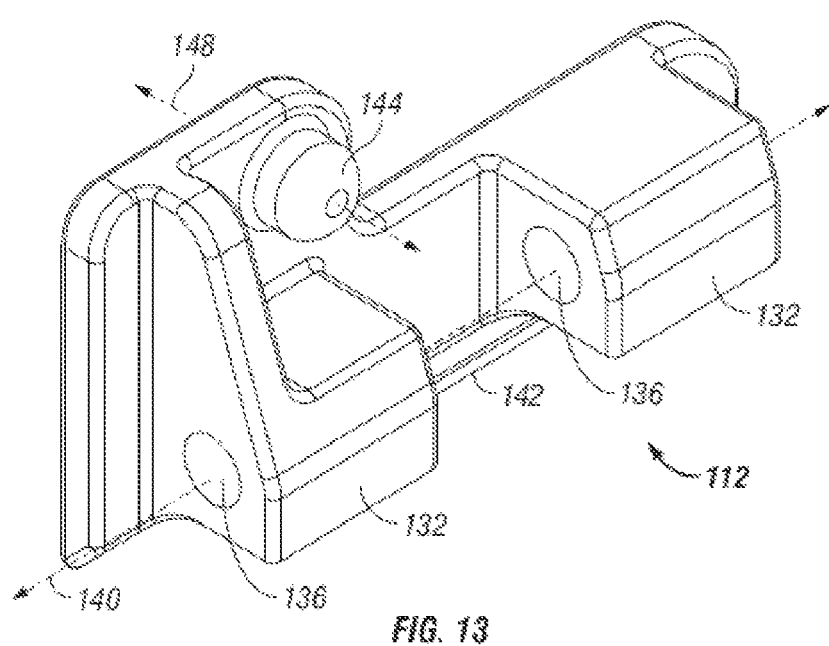

Referring to FIGS. 12 and 13, finger or flange portions 132 extend laterally inward from clamp member sidewalls 134 and define a hole 136 extending longitudinally therethrough. Clamp members 110, 112 may be assembled with flange portions 132 overlapping laterally and with holes 136 aligned to receive a pin 138 and defining a pivot axis 140. In this regard, the left and right clamp members 110, 112 may pivot with respect to each other about pin 138 and axis 140. A clamp ridge 142 may be defined along a portion of the lower edge of each clamp member 110, 112 such that when clamp members 110, 112 pivot about axis 142, ridges 142 may move towards and away from each other to hold, clamp, or fix rod 100 therebetween. According to one variation, rod 100 may be clamped or held about the upper portion thereof and with clamp members 110, 112 within the profile of rod 100 such that no portion of clamp members 110, 112 extend or protrude beyond the radius of rod 100. In one embodiment, rod 100 is generally cylindrical with a generally circular cross section and clamp members 110, 112 engage rod 100 on an upper portion of the rod spaced from the midline or diameter of the rod. In this regard, when clamp members 110, 112 are in a clamping position to clamp or hold rod 100, they are generally spaced apart a distance less than the diameter of the rod. It may be appreciated that as a result of such a design, rod 100 may be loaded directly into an anchor receiver member at the rod clamping location without requiring additional space or room to allow the clamp members to enter therein. Those skilled in the art may appreciate that such a feature may be advantageous in facilitating the use of legacy anchors or screws without the requirement that receiver portions be especially sized and dimensioned and/or retrofitted to accommodate clamp members 110, 112.

Figure 14:
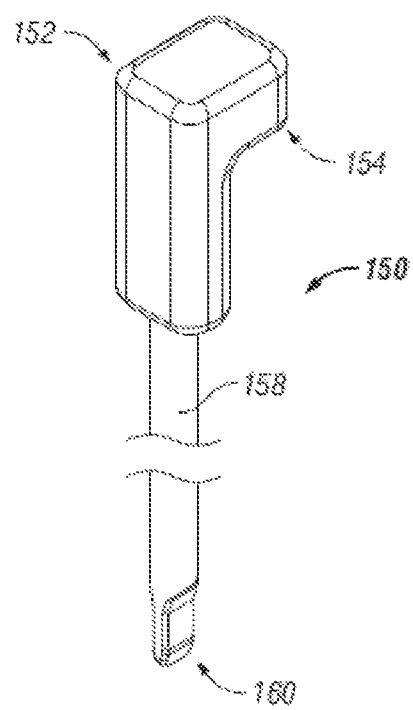
FIG. 14 is a perspective view of a longitudinal pin assembly.
Figure 15:
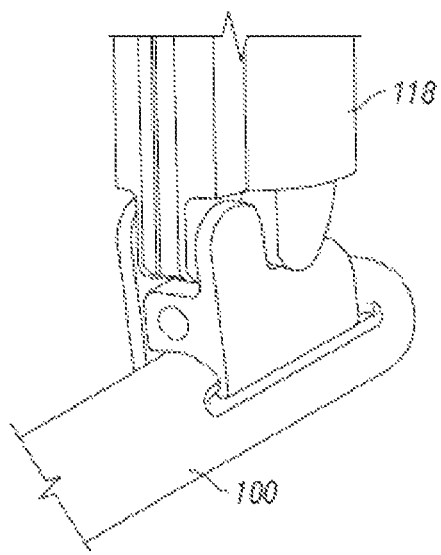
FIG. 15 is an enlarged partial perspective view of the insertion device of FIG. 2 shown in a first position.
Figure 16:
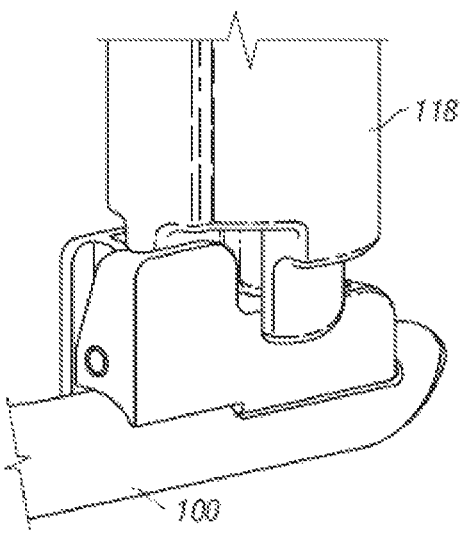
FIG. 16 is an enlarged partial perspective view of the insertion device of FIG. 2 shown in a second position.
Figure 17:
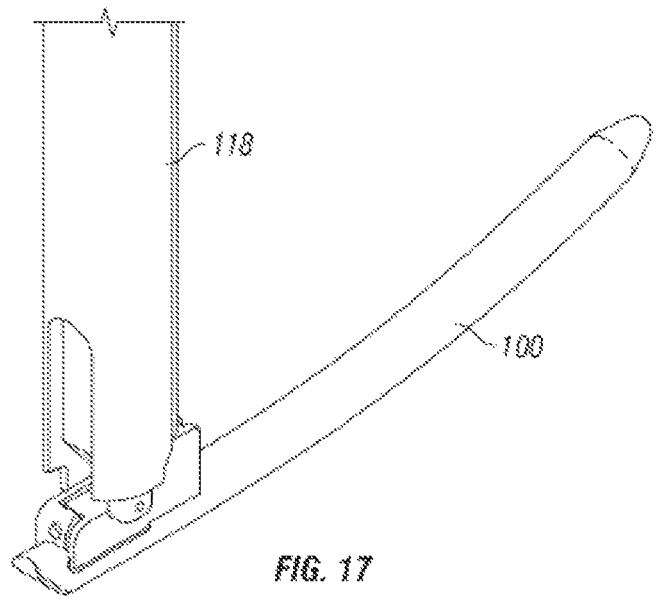
FIG. 17-18 are side and rear partial perspective views of the insertion device of FIG. 2 shown in the second position.
Figure 18:
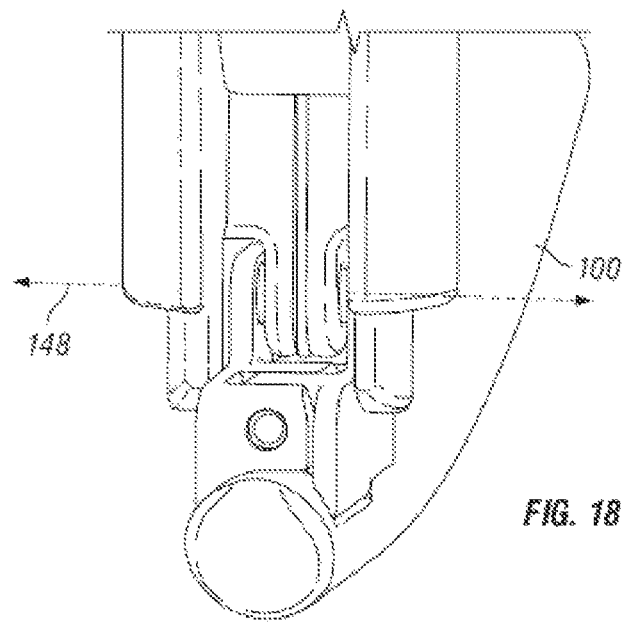

Clamp members 110, 112 may be pivoted about axis 140 or actuated to clamp rod 100 remote from the distal end 114 via pin assembly 150 that extends through guide tube 118. Referring to FIG. 14, in one variation a proximal end 152 of the pin assembly has a block or finger portion 154. As shown in FIG. 8, finger portion 154 is configured to engage an interior of thumb nut 156 such that as the thumb nut is rotated, the pin assembly 150 may be linearly advanced or retracted as desired by a user. Thumb nut 156 is internally threaded and threadably engages collar 172. In this regard, threaded collar 172 may be axially constrained to guide tube 118 via C-clip 170. In alternate embodiments, threaded collar 172 may be integrally formed with guide tube 118 such as via welding.

Figure 19:
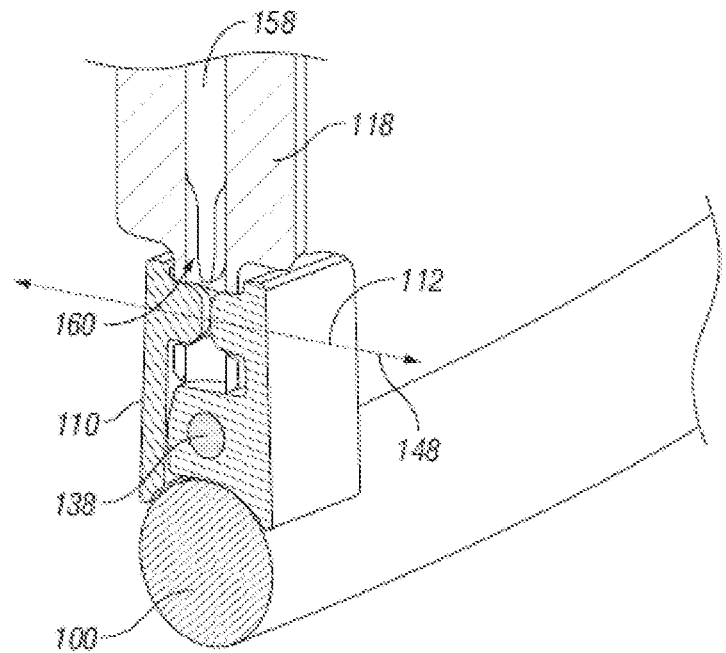
FIG. 19 is a partial cross-sectional view of the insertion device of FIG. 2, shown with the clamp assembly unclamped to the stabilization member.
Figure 20:
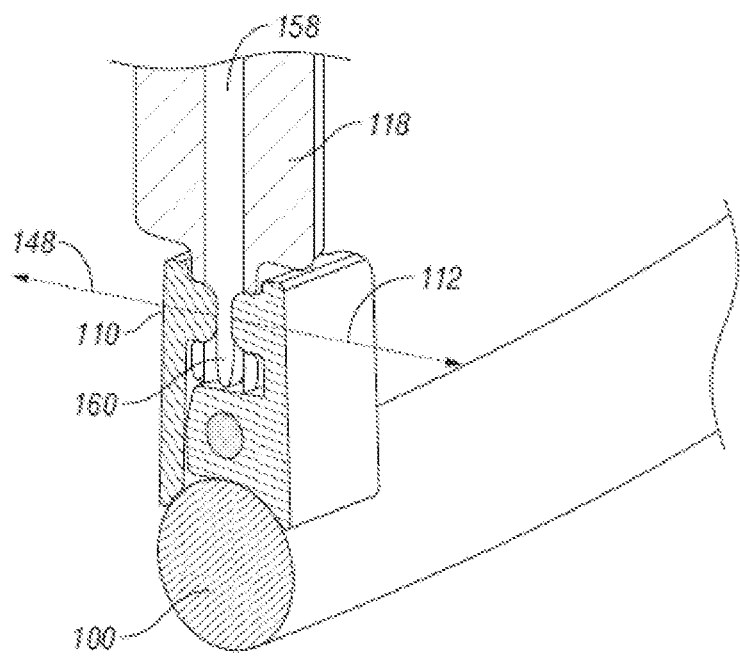
FIG. 20 is a partial cross-sectional view of the insertion device of FIG. 2, shown with the clamp assembly clamped to the stabilization member.

As best seen in FIGS. 19-20, pin assembly 150 is axially moveable within guide tube 118 and the distal end of pin 158 is configured to engage clamp members 110, 112 to cause the clamp members to pivot about axis 140. In a first position, shown in FIG. 19, the distal most tip 160 of pin 158 is spaced from the distal most end 114 of tube 118 and spaced distally from between protrusions 144 of clamp members 110, 112. In this position, clamp members 110, 112 may pivot apart such that rod 100 is not clamped therebetween. Referring to FIG. 20, pin assembly 150 may be advanced to a second position, shown in FIG. 20, with the distal most tip 160 of pin 158 advanced distally between protrusions 144. In this second or clamped position, the ridges 142 of clamp members 110, 112 may move towards each other to clamp or hold rod 100 therebetween.

A protrusion 144 extends inward from each clamp member sidewall, respectively. Protrusions 144 are generally cylindrical with rounded free ends configured and dimensioned to linkingly engage openings provided in the distal end of insertion device 10. Protrusions 144 are generally coaxially positionable within openings 146 and aligned along a pivot axis 148 defined through the center thereof. Pivot axis 148 extends generally perpendicular to a central axial plane of rod 100 and clamp pivot axis 140. In this regard, when assembled to device 10, clamp members 110, 112 are axially fixed and rotatable about the distal end thereof such that when rod 100 is clamped therebetween, rod 100 may pivot about axis 148 during installation in a patient.

One embodiment of a means for controllably actuating, pivoting, or rotating the stabilization member 16 about the distal end of insertion device 10 generally comprises a first member and a second member, wherein the first member is linearly translatable with respect to the second member along the longitudinal axis of the device and the stabilization member is linkingly engaged to the first member and rotatably engaged to the second member. When the first member is translated with respect to the second member along the longitudinal axis, the stabilization member rotates about the second member. According to one embodiment, shown in FIG. 8, stabilization member insertion device 10 generally comprises an outer guide tube 118 and a pusher assembly 116 concentrically disposable within screw extension or sleeve 50 to position a stabilization member 16 in relation to the attached screw(s).

As best seen in FIG. 8, pusher assembly 116 generally comprises a pusher member 160 integral to a threaded drive shaft or stein portion 162. Pusher assembly 116 is configured and dimensioned to fit within outer tube 118 such that it is moveable with respect to outer tube 118 along a longitudinal axis 164. A knob 166 is internally threaded to mate with external threads of drive shaft 162 Such that rotation of knob 166 causes linear translation of pusher assembly 116 with respect to outer guide tube 118 along axis 164. Pusher member 116 includes a distal end 168 configured and dimensioned to pushingly and/or slidingly engage proximal end 102 of rod 100.

In operation, when knob 166 is rotated, drive shaft 116 is moved downward or in the distal direction along axis 164 and distal end 168 of pusher member 116 pushes or drives the proximal end 102 of rod 100 downward or in the distal direction and causes rod 100 to rotate or pivot about pivot axis 148. In this regard, referring to FIGS. 21-24, rod 100 is moveable from a generally upright orientation or position or a position wherein axis 106 is aligned with or parallel to axis 164 (FIG. 21) to a more horizontal orientation or position or a position wherein axis 164 is perpendicular or angled with respect to axis 106 (FIG. 24). Thus, rod 100 may be advanced through sleeve 50 and installed in a patient utilizing a minimally invasive approach. As described above, in one embodiment stabilization member 16 is rotatably actuatable by insertion device 10 independent of movement along the axis of the sleeve, i.e., the stabilization member 16 may be rotated by insertion device 10 anywhere along the length of the sleeves 22, 24.

A handle 180 may be provided to facilitate insertion of device 10 into sleeves 22, 24. A longitudinal or axial stop may be provided along the exterior of insertion device 10 to ensure that the insertion device and rod attached thereto extends a sufficient length into sleeves 22, 24, such that rod 100 may be positioned sufficiently proximate to anchors 12, 14 attached to the distal ends of sleeves 22, 24.

Figure 25:
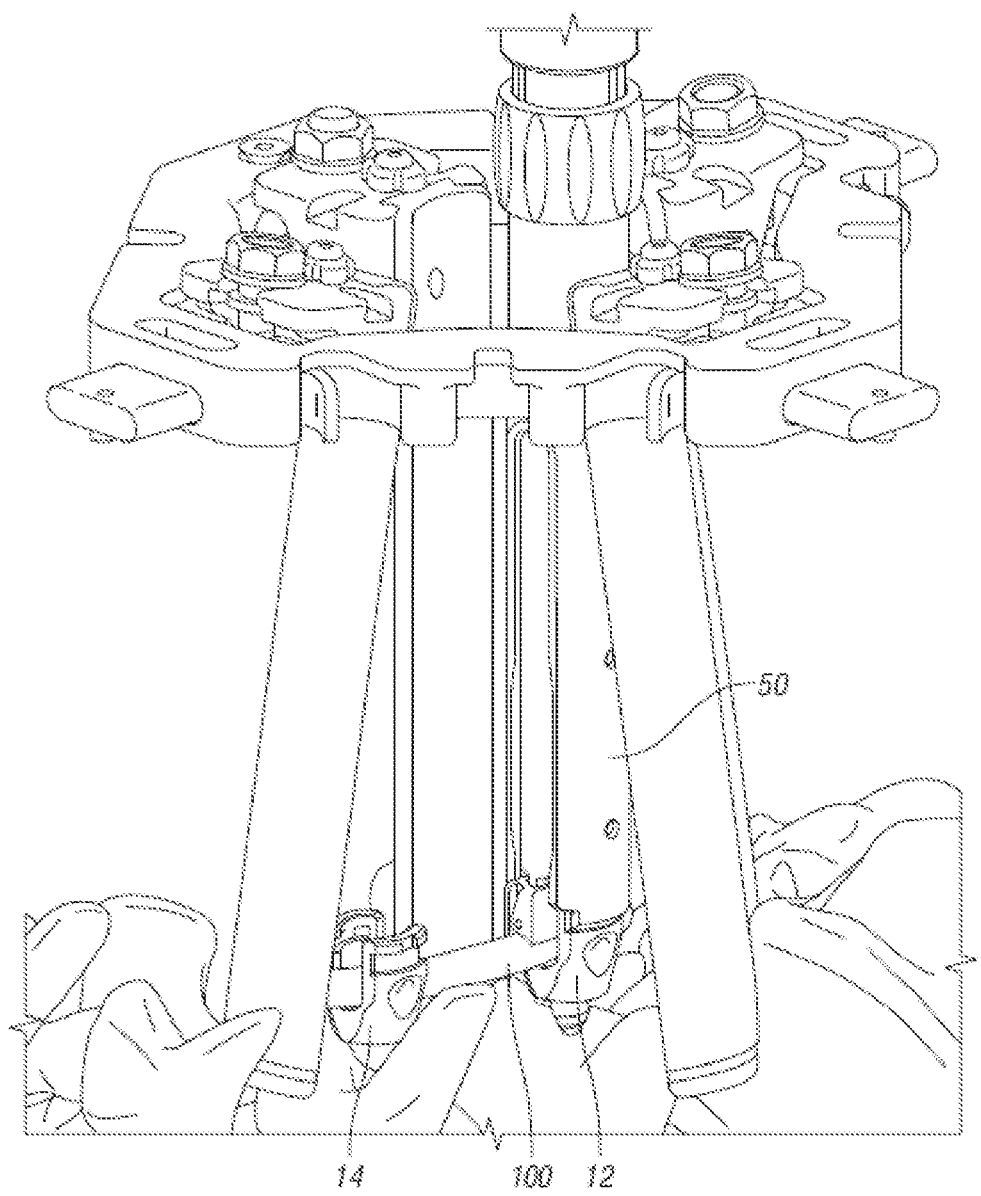
FIG. 25 is a perspective view of another embodiment of a stabilization member and insertion device shown during another embodiment of an installation method according to the present invention.

Surgical techniques or methods using the above described system and device will now be described. According to one embodiment of the present invention, anchors 12, 14 may be implanted into the vertebrae percutaneously, minimally invasively, or through an open or mini-open procedure. In one exemplary embodiment, at least one of the anchors 12, 14 is attached to, mounted on, or retained in sleeve 50, and the sleeve 50 and attached anchor are inserted through an open incision, a tube or cannula, or directly through the skin and tissue of the patient to implant the anchor into bone, such as the pedicles of a vertebrae. In alternate embodiments, anchors 12, 14 can be implanted into bone without a sleeve 50 attached thereto, and sleeve 50 may be mounted on an anchor after it is implanted. For example, as shown in FIG. 25, according to one embodiment, anchors 12, 14, may be installed utilizing a retractor system 190, and one of the anchors 12, 14 may have a sleeve attached thereto while one or more additional anchors does not have a sleeve attached. One exemplary retractor system 190 that may be utilized is disclosed in U.S. patent application Ser. No. 11/422,511, the entire contents of which are incorporated herein by reference. In another exemplary embodiment, shown in FIG. 1, both anchors 12, 14 may have a sleeve attached thereto.

Any imaging system known to those skilled in the art may be utilized to determine and locate optimum placement and orientation of the anchors in the vertebrae and/or to identify locations for entry of the anchors. Other methods known by skilled artisans for locating and placing anchors 12, 14 into the vertebrae may be also used, including, but not limited to, a CT scan or x-ray, any known viewing instrument or apparatus, endoscopic, and microscopic monitoring.

Any known methods of locating and preparing the pedicle for screw implantation may be utilized. In this regard, according to one known minimally invasive technique, after location of the entrance point, instrumentation of the pedicle may begin with the insertion of a cannulated needle through the skin of a patient to the intersection of the facet and transverse process of a vertebral body to which an anchor is to be implanted. A Kirschner wire or guidewire may be inserted through the needle cannula and into the pedicle. Successive dilation cannulas may be subsequently inserted over the guidewire to dilate the fascia and muscle until a working cannula is large enough to accommodate anchor 12 or 14. All but the largest cannula may be removed from the working cannula to expose a passageway through the skin to the pedicle or insertion site. In one embodiment, a hole in the pedicle may be prepared by placing a cannulated drill and/or tap over the guidewire and through the working cannula to prepare the pedicle for screw insertion. In other embodiments, the pedicle may be prepared with other instruments known in the art, including but not limited to an awl, a trocar, and a needle.

Any known methods of installing a pedicle screw into a prepared pedicle may be utilized. In this regard, according to one known minimally invasive technique, a cannulated anchor, such as screw 32 attached to sleeve 50, may be placed over the guidewire and advanced through the working cannula to the prepared pedicle. A driving tool such as a cannulated screw driver may be used to rotate screw 32 and threadedly engage screw 32 to the bone. Sleeve 50 may follow screw 32 to the bone and the screw driver and guidewire may be removed. The working cannula may also subsequently be removed, leaving the sleeve 50 and screw 32 secured to the bone.

With the anchors 12, 14 secured to the bone and at least one sleeve 50 extending from at least one anchor, stabilization member 16 may be installed between anchors 12, 14 utilizing insertion device 10. In this regard, stabilization member 16 is positioned on insertion device 10 and may be inserted into sleeve 50 with the stabilization member 16 initially in a generally vertical position (as shown in FIGS. 21-22). As insertion device 10 is advanced in the distal direction within sleeve 50 and shaft 116 is moved in the distal direction, rod 100 rotates or pivots about pivot axis 148 to a more horizontal position (as shown in FIG. 24). In this regard, insertion device 10 moves stabilization member 16 in a distal direction toward anchors 12, 14. The proximal end of rod 100 swings outward through opening 76 of sleeve 50 and the distal tip 108 of stabilization member 100 is advanced toward the channels 26 of an adjacent anchor 14. In one exemplary embodiment, as the insertion device 10 is advanced distally into sleeve 50 and shaft 116 is advanced distally with respect to the outer guide tube 118 of insertion device 10, the tip 108 of stabilization member 100 follows a generally elliptical path entering the patient through a first opening and traveling toward the second anchor 14 and through the channel 26 of the second anchor. With rod 100 in a more horizontal position, rod 100 may be then inserted into the channel 26 of the first anchor 12 by advancing the rod insertion tool 10 distally toward the distal end of sleeve 50. According to one variation, the clamp members 110, 112 fit within channel 26 of anchor 12 such that rod 100 may be loaded into the anchor at the same axial location as the clamp members 110, 112 grip or clamp the rod. Sufficient clearance, space or room is also provided within the channel that clamp members may be radially separated apart to release or disengage rod 100 so as to leave rod 100 installed within channel 26

The clamp members 110, 112 may be unclamped from rod 100 to allow the stabilization member 16 to be removed from the insertion device. Once stabilization member 16 is placed within anchors 12, 14 to the desired position, a cap and/or set screw may be driven downward, such as through sleeve 50, to contact stabilization member 16 and fix stabilization member 16 to anchors 12, 14. In this regard, a driving tool may be placed through the central channel of sleeve 50 to tighten the cap and/or set screw against the stabilization member until the stabilization member is firmly seated in coupling element 42 of at least one of anchors 12, 14.

With reference to FIGS. 26-38, various embodiments of stabilization member insertion devices are shown. These stabilization member insertion devices may be used in open surgical procedures, mini-open surgical procedures, and/or minimally invasive surgical procedures, for example. In particular, the insertion devices may be suitable to deliver an elongate stabilization member, such as a rod, to the surgical site using, for example, an open, mini-open, percutaneous or minimally-invasive method. In addition, a retractor may be used with the surgical procedure to provide the surgeon sufficient clearance to perform the procedure and, therefore, the instruments used for such a procedure are preferably sized and designed to fit easily within the opening created during the surgery. Although various embodiments are described with reference to certain surgical procedures, it should be understood that any suitable surgical technique may be selected.

Figures 26, 27:
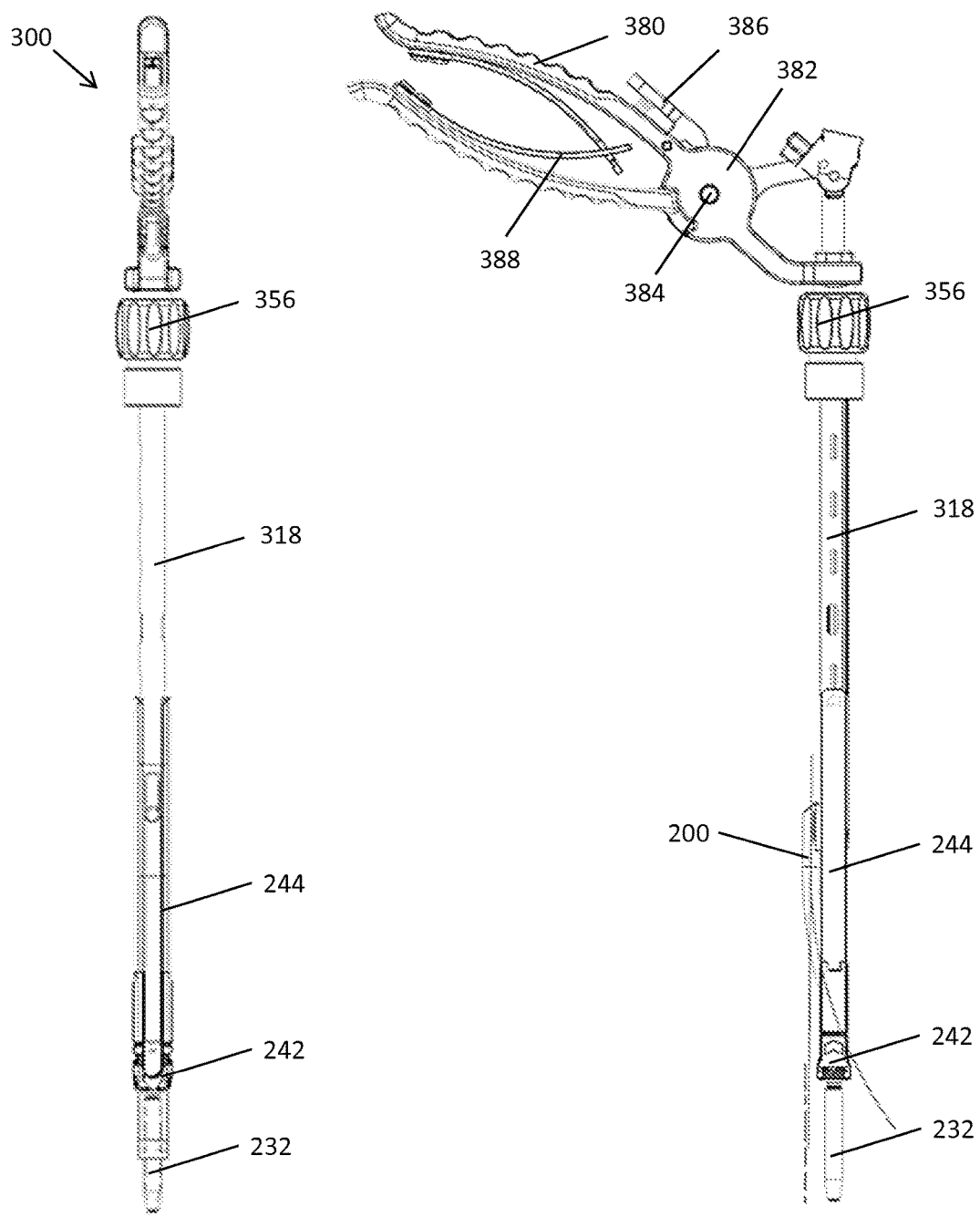
FIG. 26 is a front view of another embodiment of an insertion device.
FIG. 27 is a side view of the insertion device shown in FIG. 26.

Referring now to FIGS. 26-27, an alternative embodiment of a stabilization member insertion device 300 is shown for use in a minimally invasive vertebral stabilization system. The system may include at least one anchor 232, an elongate stabilization member 200, and the insertion device 300. The anchor 232 includes a head 234 and a shaft or shank 236, for example, having bone engaging threads. The anchors 232 may include bone fasteners, such as polyaxial screws, bone screws, hooks, etc. with a coupling element 242 attached thereto. The coupling element 242, such as a tulip element, yoke, or the like, may be provided to couple the elongate stabilization member 200 to the anchor 232. Clamp and/or wedge elements, as discussed above, may be used to secure the anchor 232 and the coupling element 242. Unlike the sleeve systems discussed above, the anchors 232 may be connected to one or more extended tabs 244. The extended tabs 244 may eliminate the need for an instrument-based sleeve by incorporating the sleeve functionality into the anchor 232. The extended tabs 244 may be separated and removed from the anchor 232 after the construct is complete.

With reference to FIGS. 28A-E, an embodiment of a coupling element 242 having extended tabs 244 is shown. One or more extended tabs 244 define an open central portion 258 and a central longitudinal axis 260. The extended tabs 244 may extend upwardly from an upper portion of the coupling element 242 and/or anchor 232. The extended tabs 244 may each have a generally elongate curved body, for example, to mimic a sleeve. The extended tabs 244 may include a pair of diametrically opposed extended tabs 244 defining opposed longitudinal openings. The longitudinal openings may provide lateral access to and from the open central portion 258. For example, a portion of the elongate stabilization member 200 may be extendable through the longitudinal openings. In addition, a portion of the insertion device 300 may be extendable through the open central portion 258. Although two extended tabs 244 are exemplified, any suitable number, shape, and design of extended tabs 244 may be utilized to provide access for the elongate stabilization member 200 and/or insertion device 300.

The extended tab 244 may be comprised of a multi-part component. For example, the extended tab 244 may include a first extension element 246 connected to the coupling element 242 and/or first anchor 232 at a break point 243 and a second extension element 248 connected to the first extension element 246. The break point 243 may allow the extension tabs 244 to be easily removed, for example, after the stabilization member 200 has been secured to the anchor 232. The second extension element 248 may be connected to the first extension element 246 at a connection point 250. The connection point 250 may include, for example, a dovetail and/or welded connection. The interior portion of the first extension element 246 may be threaded 245, for example, to accept a threaded locking cap. The interior portion of the second extension element 248 may be smooth or threaded, for example. Although two extension elements 246, 248 are exemplified, any suitable number, shape, and design of the extension elements 246, 248 may be used to create the extended tabs 244.

Figures 28A, 28B, 28C, 28D, 28E:
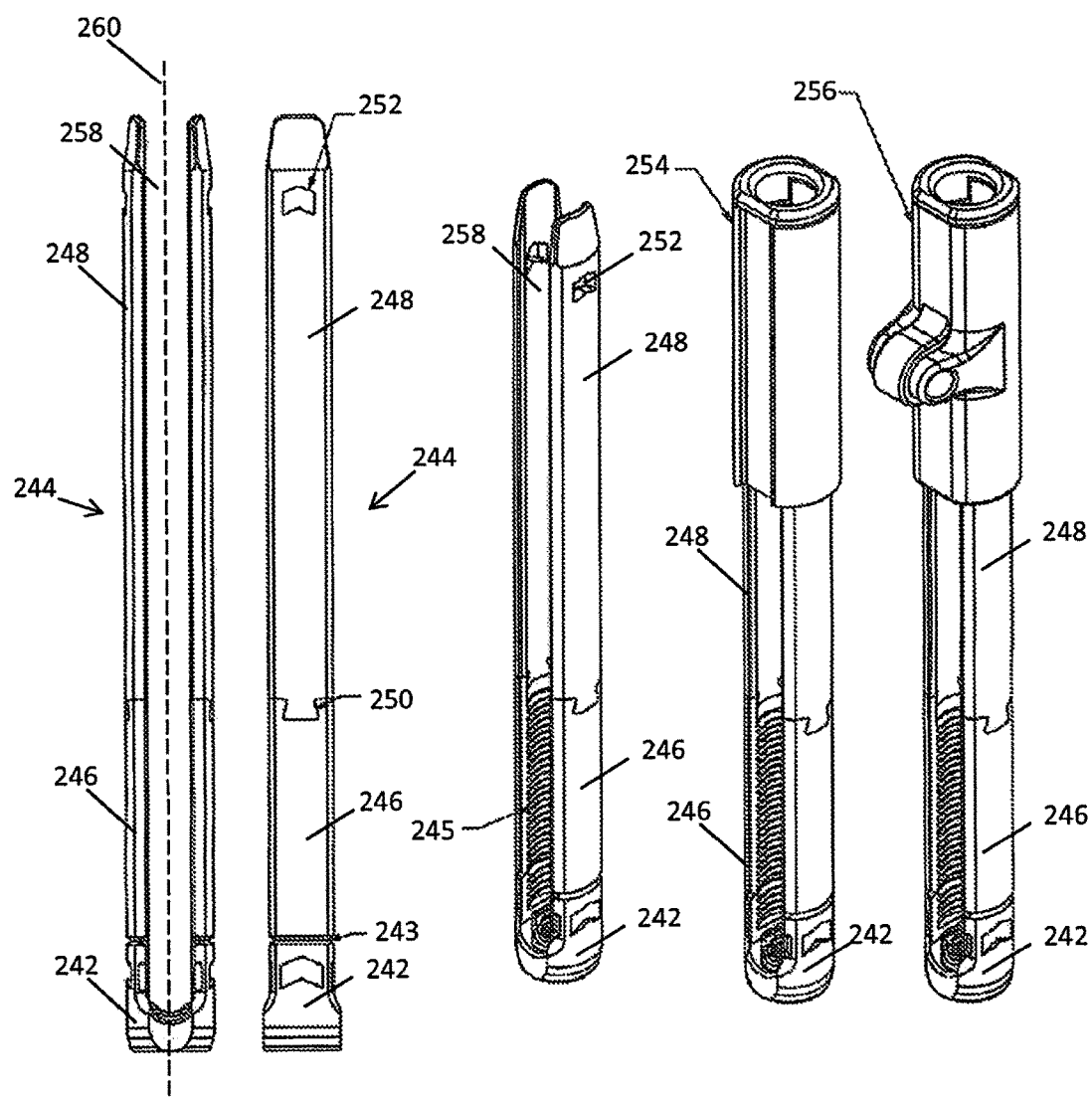
FIGS. 28A-28E depict an embodiment of a coupling element having extended tabs that may be removed after the rod is locked in place.

The extended tabs 244 may also comprise additional features, such as one or more indentations 252 to accept instrumentation, for example, for rod reduction, screw insertion, tab removal, deformity correction, or the like. As shown in FIG. 28D, a distal end of the second extension element 248 may accept a sleeve 254, for example, to provide additional structural support during rod reduction, tightening of the locking cap, compression/distraction, rod passage, general tulip manipulation maneuvers, or the like. As shown in FIG. 28E, the second extension element 248 may accept a sleeve 256 having a built-in fulcrum, for example, for use during compression/distraction maneuvers. The extended tabs 244 may be constructed to be substantially rigid, such that the tabs 244 are able to guide the insertion instrument 300 to anchor 232.

Referring to FIGS. 29A and 29B, the anchor 232 may be deliverable to a vertebral body of a patient through an opening. After the anchor 232 is secured to the vertebral body, the elongate stabilization member 200 may be inserted into the opening and articulated into position to be secured to the anchor 232. The elongate stabilization member 200 may be in the form of a rod. The rod may have a substantially straight shape or a curvilinear shape. The stabilization member 200 may have at least one indentation along its length (as shown in FIGS. 9-11), for example, such that the insertion device 300 may clampably link to the stabilization member 200 about the indentation(s). The elongate stabilization member 200 extends from a proximal end 202 to a distal end 204. A portion of the proximal end 202 may be configured and dimensioned to interact with the insertion device 300. The proximal end 202 may be angled with respect to a longitudinal axis of the stabilization member 200, and the proximal end 202 may define a concave surface.

The insertion device 300 releasably and rotatably links to the elongate stabilization member 200. FIGS. 29A and 29B show a close up view of the insertion apparatus 300 holding the stabilization member 200 with (FIG. 29A) and without (FIG. 29B) the coupling element 242 and extended tabs 244 present. The insertion device 300 is configured and dimensioned to be received between the extended tabs 244 and within the open central portion 258 such that the insertion device 300 is moveable along or substantially parallel to the central longitudinal axis 260. In particular, the guide tube 318 of the insertion device 300 may be sized and dimensioned to be received within the open central portion 258 and between the extended tabs 244. The elongate stabilization member 200 is deliverable in a first orientation substantially parallel to the central longitudinal axis 260.

Instead of positioning the elongate stabilization member 200 through the open central portion 258, the elongate stabilization member 200 may be offset from the insertion device 300. The elongate stabilization member 200 may be cantilevered off the insertion device 300 such that at least a portion of the elongate stabilization member 200 is positioned outside the extended tabs 244. In particular, at least a portion of the elongate stabilization member 200 is not positioned within the open central portion 258 and is positioned outside the extended tabs 244 and outside the open central portion 258. For example, the proximal end 202 of the elongate stabilization member 200 may not be contained within the open central portion 258 in the first orientation. Although a curved rod is depicted and a distal end 204 may enter the open central portion 258, if a straight rod were used instead, the distal end 204 would not enter the open central portion 258 and would remain completely outside the extended tabs 244 and outside the open central portion 258.

Figure 30A:
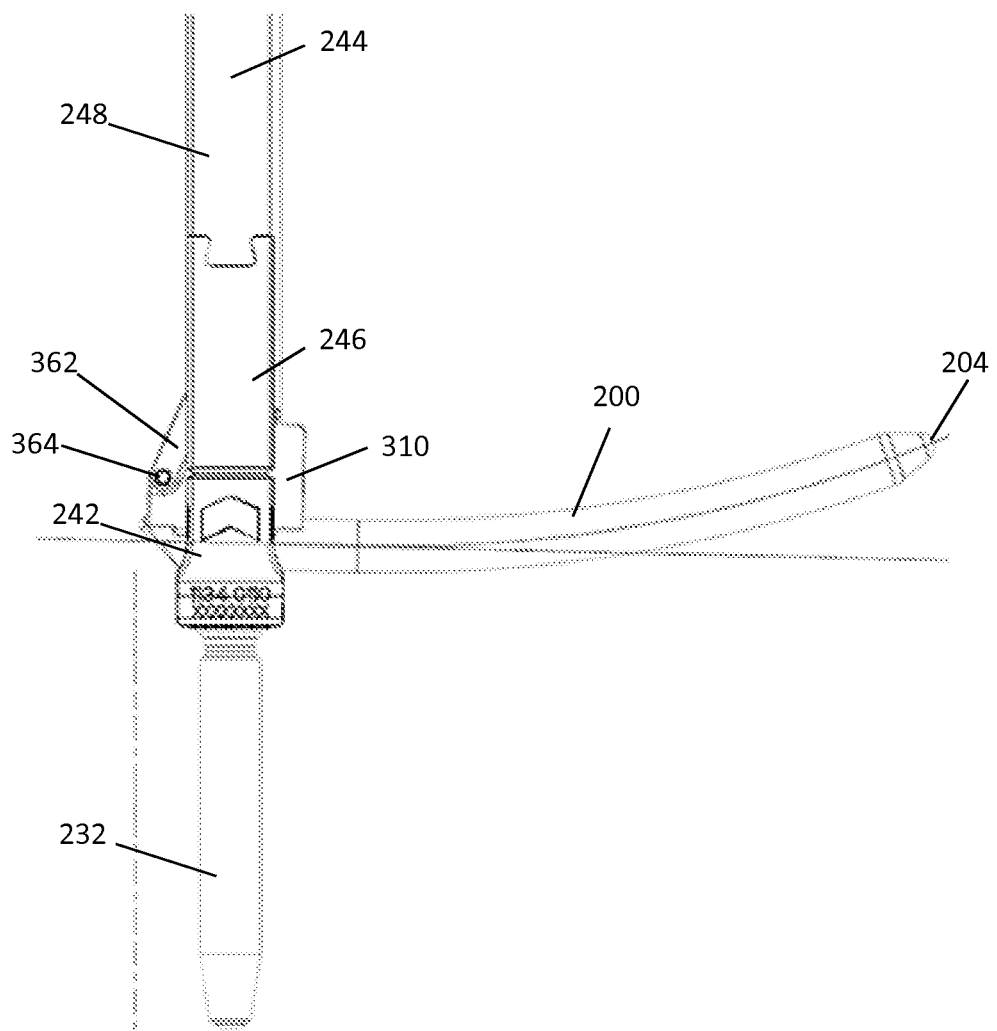
FIGS. 30A and 30B are close-up side views of the insertion apparatus shown in FIG. 27 with the elongate rod articulated 90° with (FIG. 30A) and without (FIG. 30B) an extended tab and tulip present.
Figure 30B:
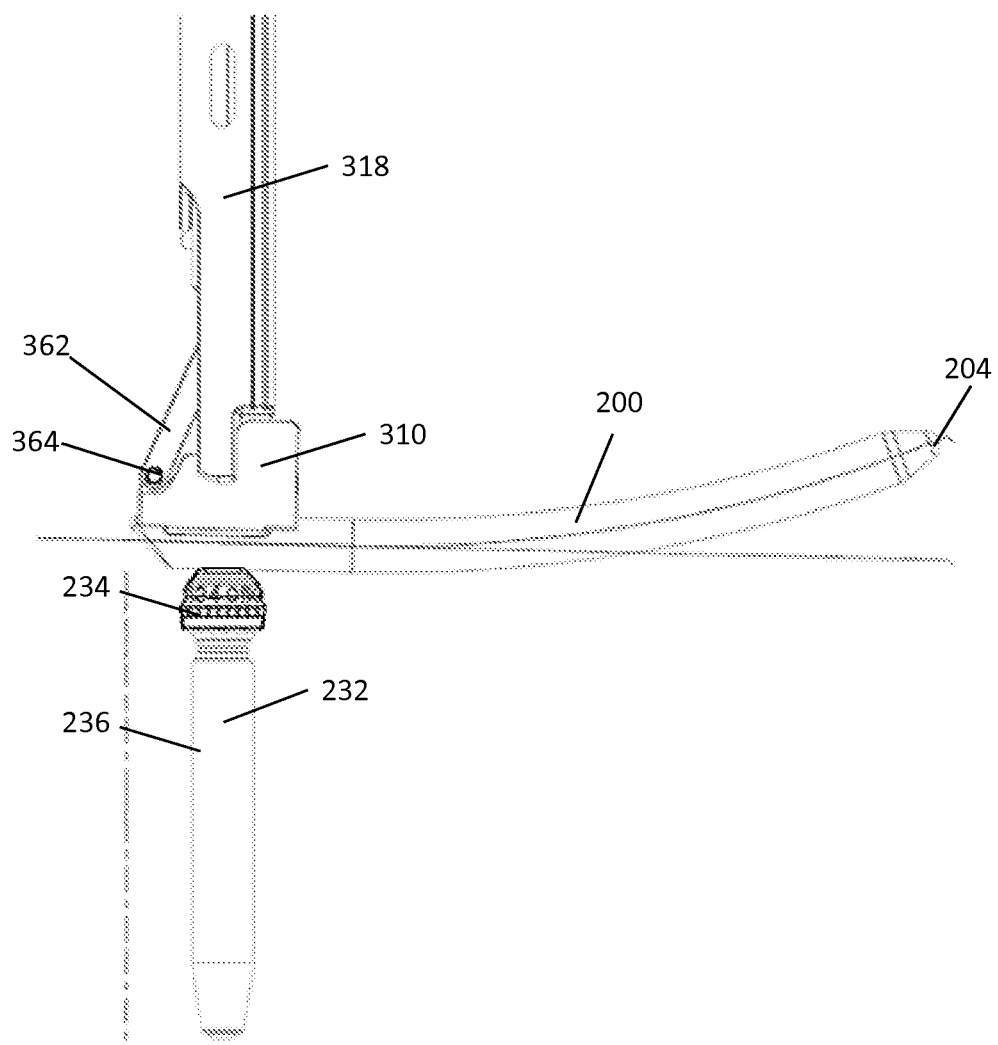

Independent of movement of the insertion device 300 along or substantially parallel to the central longitudinal axis 260, the elongate stabilization member 200 is rotatably actuatable by the insertion device 300 to extend in a second orientation angled with respect to the first orientation to position the stabilization member 200 in relation to the first anchor 232. The second orientation may be angled at about 90° relative to the first orientation, for example. FIGS. 30A and 30B are close-up side views of the insertion apparatus 300 with the elongate stabilization member 200 articulated 90° with (FIG. 30A) and without (FIG. 30B) the extended tab 244 and coupling element 242 present. As is evident, the stabilization member 200 is pivoted into a position to be attached to the anchor 232, for example, using coupling element 242. The insertion and articulation of the elongate stabilization member 200 may be controlled with the use of fluoroscopy, for example, to help guide axial and rotation movements.

Once in position, a locking cap may be used to secure the stabilization member 200 in the coupling element 242. The stabilization member 200 should be seated firmly in the coupling element 242 in order for the elements of the fixation device to be properly secured. The extended tabs 244 may be removed, for example, after the elongate stabilization member 200 is locked in place.

Figure 31A:
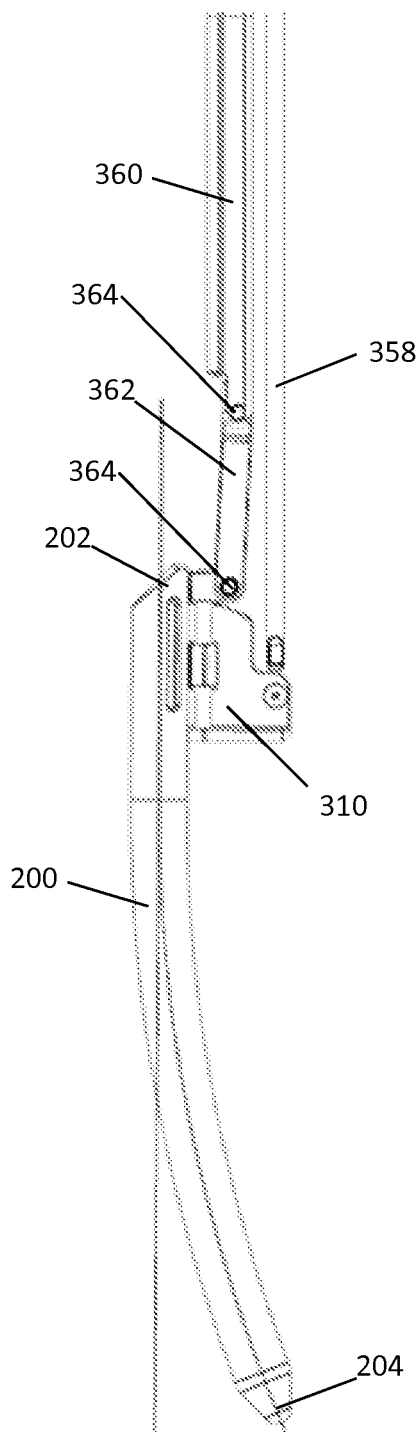
FIGS. 31A and 31B are close-up side views of the insertion apparatus shown in FIG. 27 with the elongate rod in the initial 0° position with the pin in a first position enabling the clamp members to pivot apart (FIG. 31A) and with the pin in a second position enabling the clamp members to securely hold the rod (FIG. 31B)
Figure 31B:
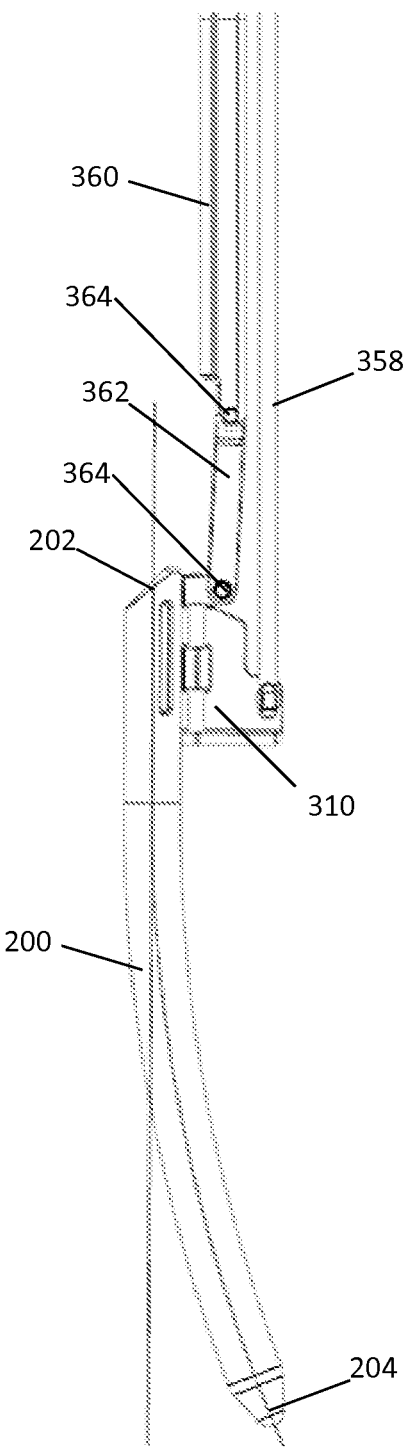

The insertion device 300 may be operable to place the stabilization member 200 between one or more anchors 232. The insertion device 300 may include an outer guide tube 318 having a pusher member 360 and/or a pin assembly including a pin 358 extending therethrough. FIGS. 31A and 31B are close-up side views of the insertion apparatus 300 with the guide tube 318 removed. The pusher member 360 may be configured to enable pivoting of the elongate stabilization member 200. The pin assembly including pin 358 may be configured to enable locking and unlocking of the elongate stabilization member 200 to the insertion device 300.

Similar to the clamp members discussed above, the elongate stabilization member 200 may be releasably clampable to the insertion device 300 between first and second clamping members 310, for example, at a clamping location spaced from a midline of the elongate stabilization member 200. As described for FIGS. 12 and 13 above, the first clamping member 310 may include a first generally cylindrical protrusion insertable into a distal portion of the insertion device 300 and the second clamping member 310 may include a second generally cylindrical protrusion insertable into the distal portion of the insertion device 300. The first and second clamping members 310 may be coupled by a pin extending through a first and second opening in the first and second clamping members 310, respectively.

In operation, the stabilization member 200 may be attached to the clamping members 310 of the insertion device 300 in the first, insertion orientation, which is shown in FIG. 31A in an unlocked position. The clamping members 310 may be locked into position by actuating the pin assembly. In particular, thumb nut 356 may be rotated in a first direction to linearly advance the pin 358 and engage the clamping members 310, which is shown in FIG. 31B. The thumb nut 356 may be internally threaded to threadably engage the pin 358.

Figure 32A:
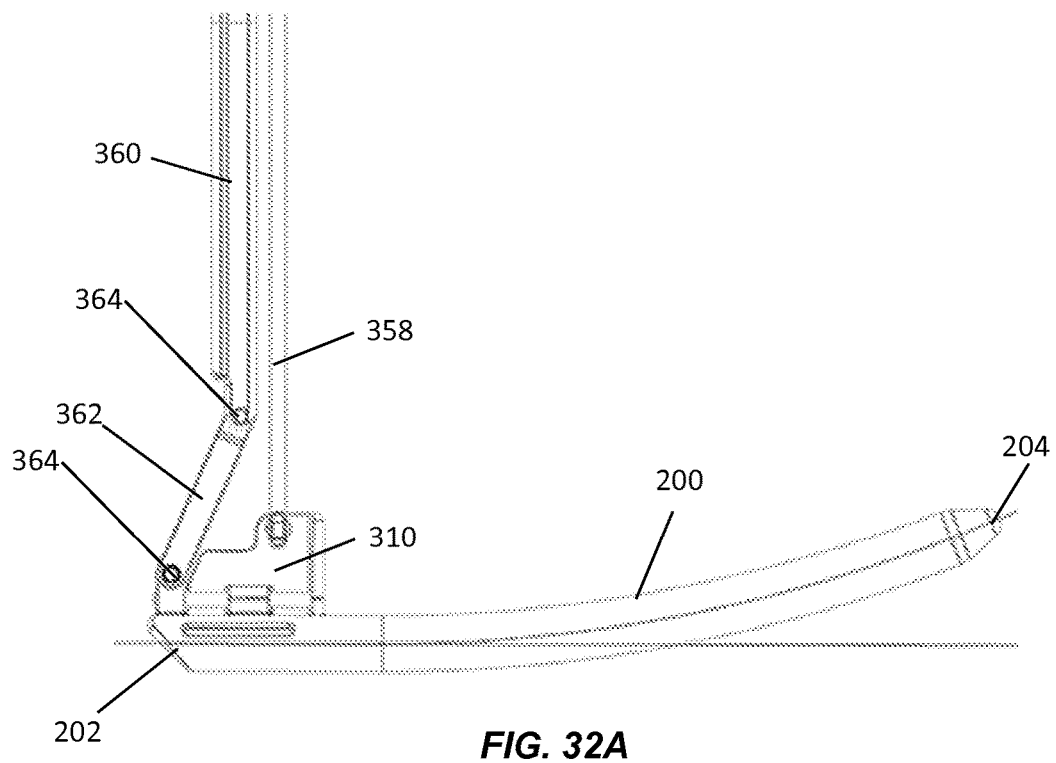
FIGS. 32A and 32B are close-up side views of the insertion apparatus shown in FIG. 27 with the elongate rod articulated 90° with the pin in the second position securely holding the rod (FIG. 32A) and with the pin in the first position allowing the rod to be released (FIG. 32B)

After the stabilization member 200 is locked in place, the stabilization member 200 may be pivoted into the second, deployed position as shown in FIG. 32A. A user may pivot the stabilization member 200 by squeezing handles 380 of the insertion device 300 together. When a user squeezes the handles 380, the pusher member 360 is advanced linearly to move linking member 362, which is coupled to the clamping members 310, thereby pivoting the stabilization member 200. The pusher member 360 may be coupled to the linking member 362 with coupling member 364. Similarly, the linking member 362 may be coupled to the clamping member 310 with another coupling member 364. As shown in FIG. 27, the insertion device 300 may include a ratchet 382 coupled to the insertion device by coupling member 384. The coupling members 364, 384, which act as pivot points, may include pins, for example. The ratchet 382 may be in the shape of a wheel having a plurality of teeth positioned around the periphery. The ratchet 382 may be uni-directional to provide for controlled articulation of the stabilization member 200. The ratchet 382 may be locked by a locking member 386, for example, having corresponding teeth designed to engage the teeth of the ratchet 382 when depressed. In addition, the handles 380 may be provided with one or more spring elements 388 to control the pivoting mechanism and allow the handles 380 to maintain an expanded position unless a force is applied.

Figure 32B:
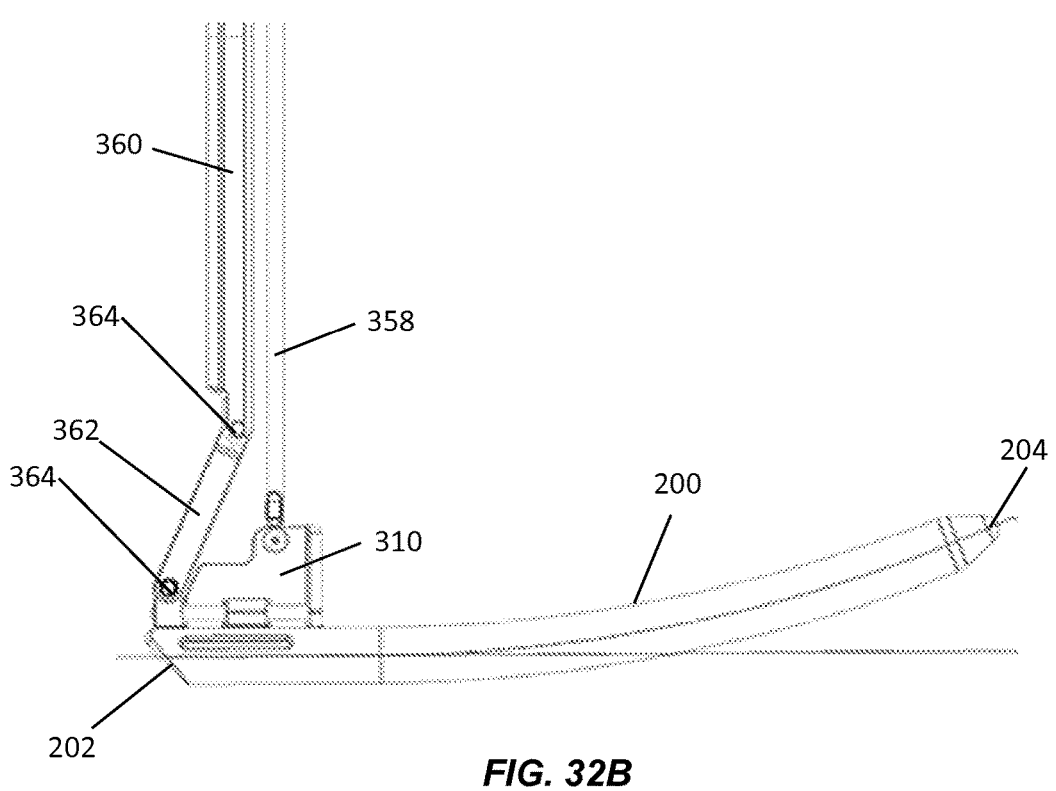
Figures 33A, 33B:
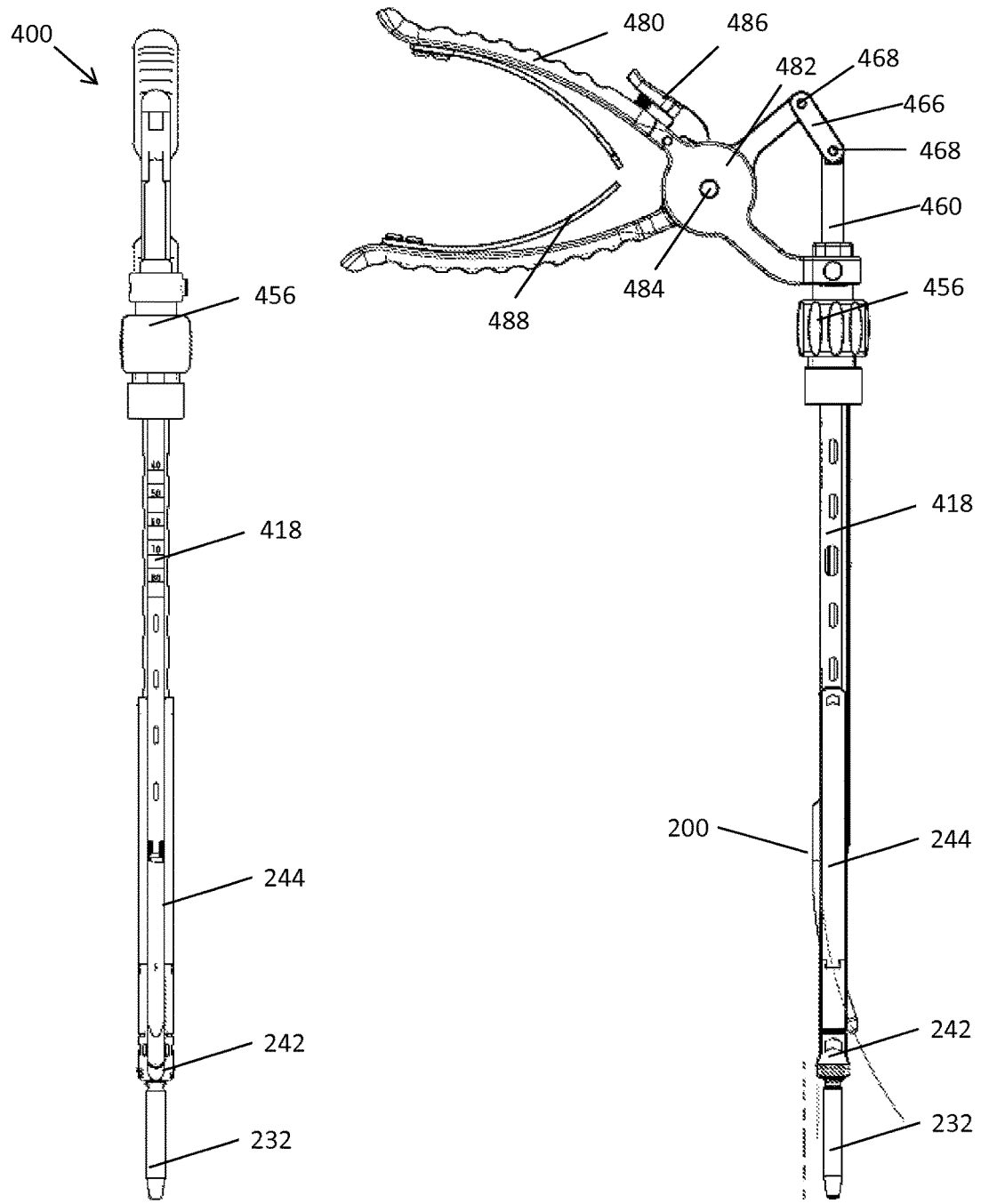
FIGS. 33A-33C are front, side, and cross-sectional views, respectively, of another embodiment of an insertion device.
Figure 33C:
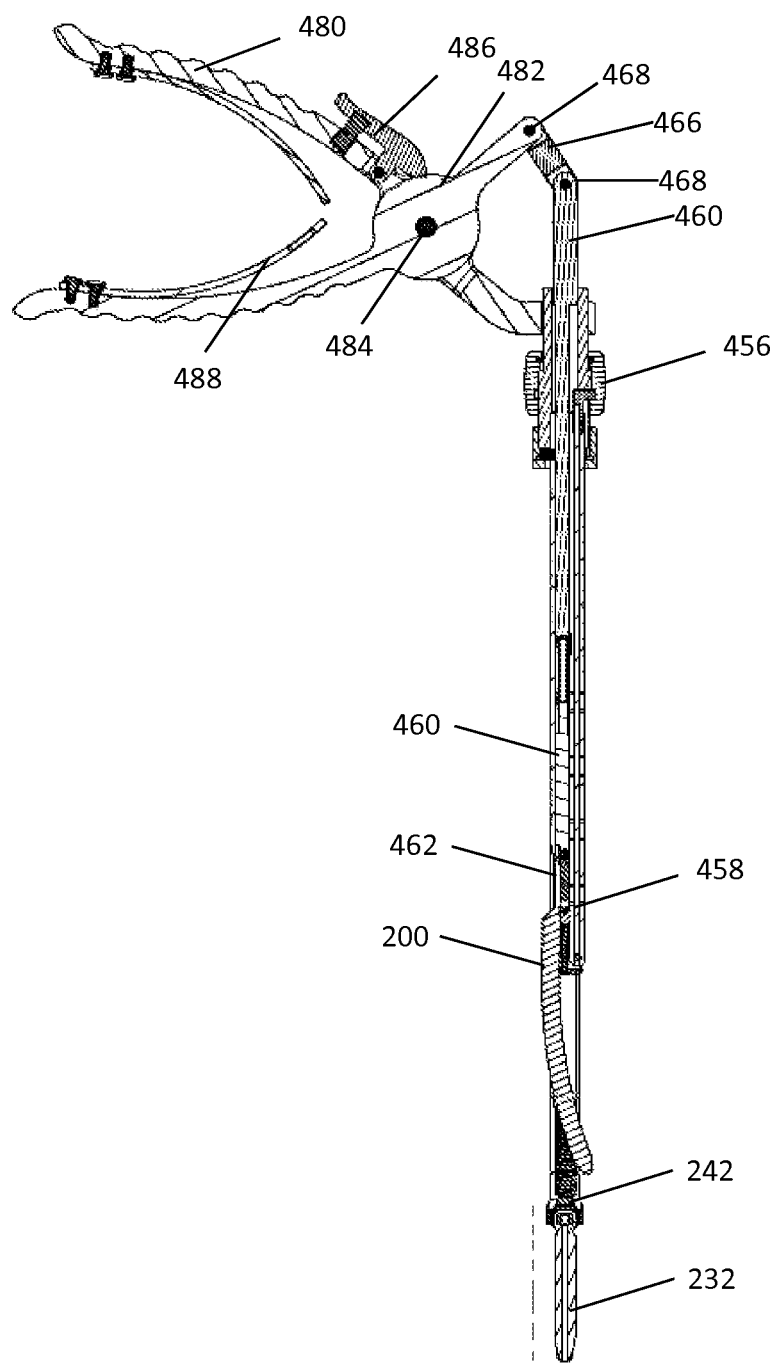

After the stabilization member 200 is positioned in the coupling element 242 and optionally coupled thereto (e.g., with a locking cap), the clamping members 310 may be unlocked by actuating the pin assembly in the opposite direction. In particular, thumb nut 356 may be rotated in a second direction, opposite to the first direction, to linearly retract the pin 358 and disengage the clamping members 310, which is shown in FIG. 32B. The stabilization member 200 may then be released and removed from the insertion device 300, and the insertion device 300 may be removed from the patient. If not already secured, the stabilization member 300 may be secured to the anchor or anchors 232 to complete the construct.

Referring to FIGS. 33-36, another embodiment of an insertion device 400 is provided. Insertion device 400 is substantially similar to insertion device 300 except that the handles 480 are coupled to the pusher member 460 with an additional linking member 466. FIGS. 33A-C show alternate views of the insertion device 400 with the stabilization member 200 in the first, insertion orientation. The insertion device 400 may include an outer guide tube 418 having the pusher member 460 and/or pin assembly including pin 458 extending therethrough. The guide tube 418 may include a series of markings, as shown in FIG. 33A, to identify depth, for example. FIGS. 34A and 34B show the insertion device 400 with the stabilization member 200 in the second, articulated orientation.

Figure 34A:
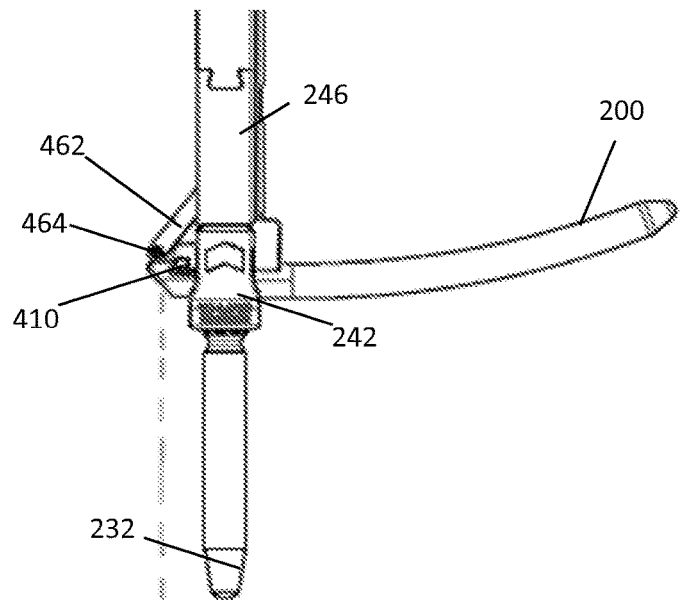
FIGS. 34A and 34B are close-up side and cross-sectional views, respectively, of the insertion apparatus shown in FIG. 33B with the elongate rod articulated 90°.
Figure 34B:
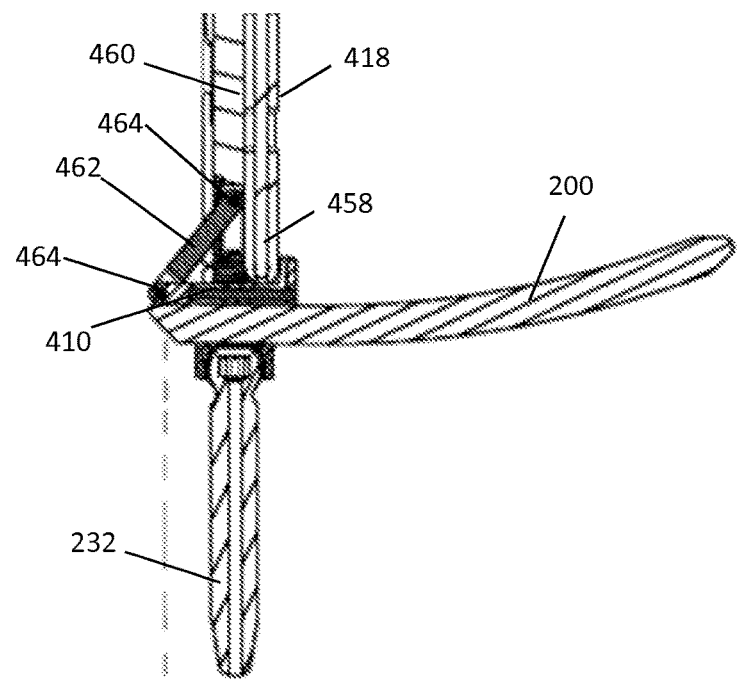
Figure 35A:
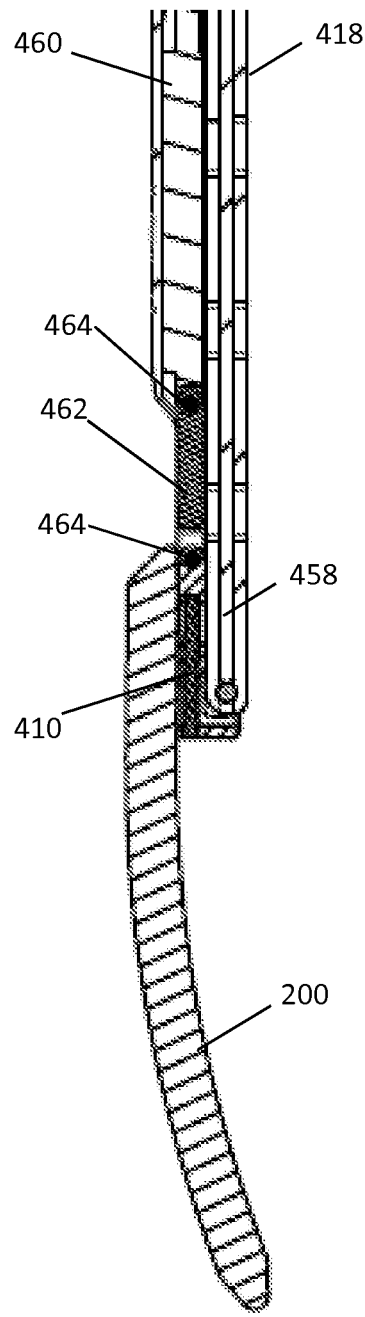
FIGS. 35A and 35B are cross-sectional views of the insertion apparatus shown in FIG. 33B with the elongate rod in the initial 0° position with the pin in a first position enabling the clamp members to open (FIG. 35A) and with the pin in a second position enabling the clamp members to securely hold the rod (FIG. 35B)
Figure 35B:
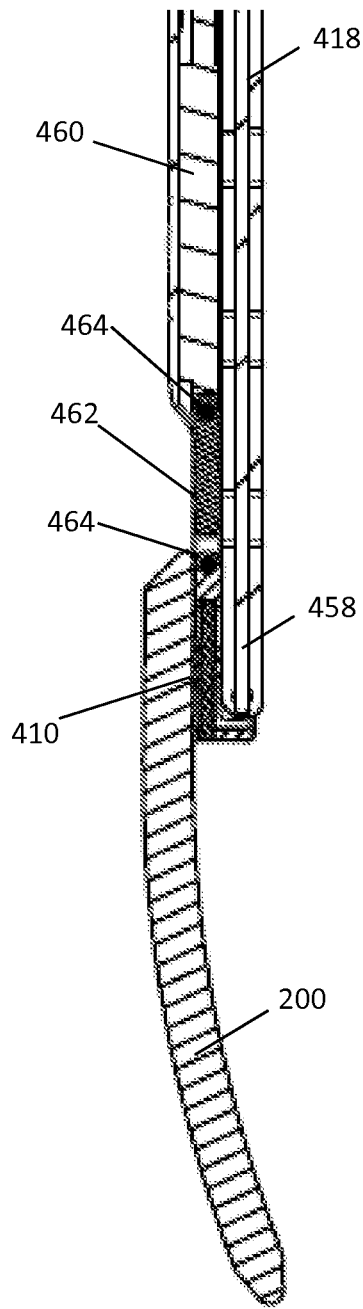
Figure 36A:
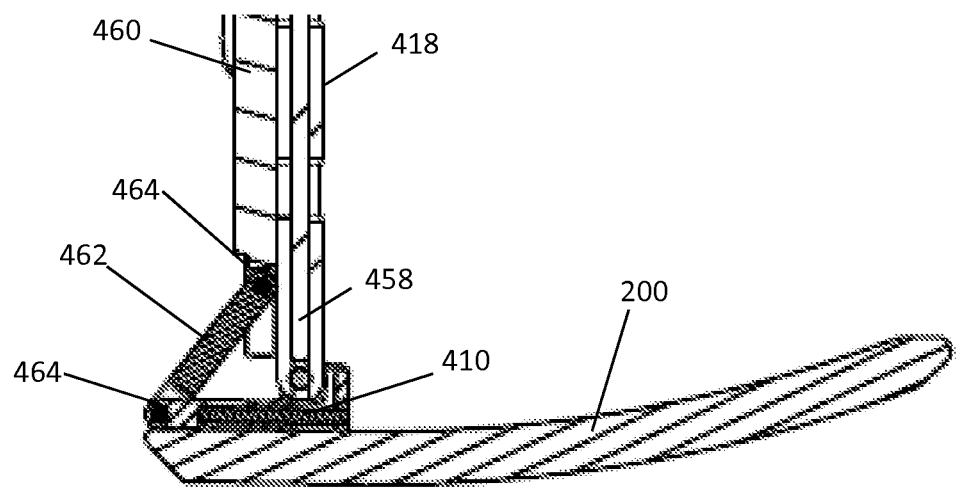
FIGS. 36A and 36B are cross-sectional views of the insertion apparatus shown in FIG. 33B with the elongate rod articulated to about 90° with the pin in a first position enabling the clamp members to open (FIG. 36A) and with the pin in a second position enabling the clamp members to securely hold the rod (FIG. 36B)
Figure 36B:
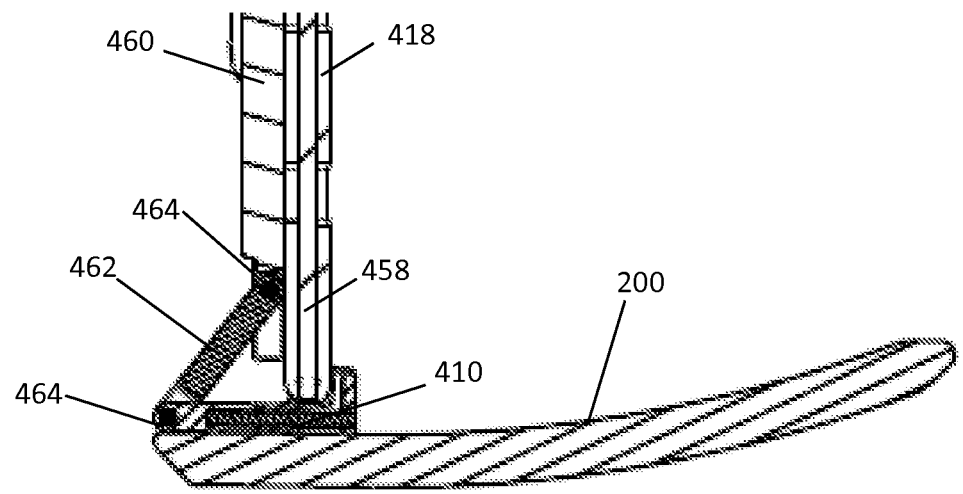

The pin assembly including pin 458 may be configured to enable locking and unlocking of the elongate stabilization member 200 to the insertion device 400. FIG. 35A shows the pin 458 in an unlocked position. The thumb nut 456 may be rotated to linearly advance the pin 458, engage the clamping members 410, and lock the stabilization member 200 to the device 400, which is shown in FIG. 35B. FIGS. 34B and 36B show the pin in a locked position with the stabilization member 200 articulated about 90°. The pin 458 may unlock the clamping members 410, which is shown in FIG. 36A, by rotating the thumb nut 456 in the opposite direction.

The pusher member 460 may be configured to enable pivoting (e.g., from about 0° to) 90° of the elongate stabilization member 200 from the insertion orientation to the final, installation orientation. The pusher member 460 may be advanced linearly to move linking member 462, which is coupled to the clamping members 410. The pusher member 460 may be coupled to the linking member 462 and the linking member 462 to the clamping member 410 with coupling members 464. The pusher member 460 may be advanced using handles 480, which are connected using a ratchet 482 affixed by coupling member 484, which acts as a pivot point. The ratchet 482 may include a uni-directional ratchet, for example, in the shape of a wheel having a plurality of teeth positioned around the periphery. The ratchet 482 may be locked by a locking member 486, for example, having corresponding teeth designed to engage the ratchet 482 when depressed.

One of the handles 480 may be coupled to the pusher member 460 by linking member 466. The other handle 480 may be coupled to a portion of the sleeve or outer guide tube 418. The linking member 466 may be attached to the handle 480 and/or the pusher member 460 by one or more coupling members 468. The coupling members 464, 468, 484, which act as pivot points, may include pins, for example. The linking member 466 may be provided, for example, to assist with disassembly and/or cleaning of the device 400. In addition, the handles 480 may be provided with one or more spring elements 488 to control the pivoting mechanism and allow the handles 480 to maintain an expanded position unless a force is applied.

Figure 37A:
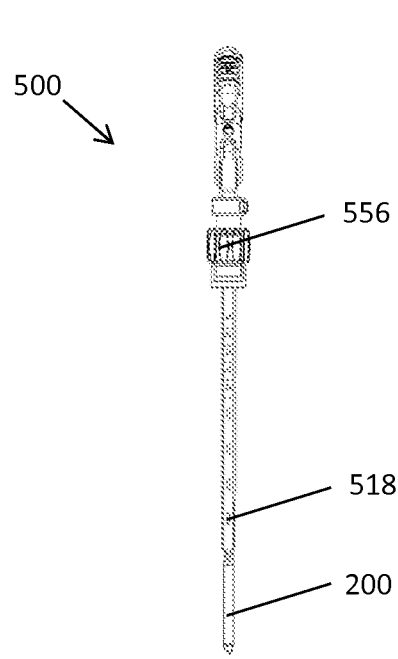
Figure 37B:
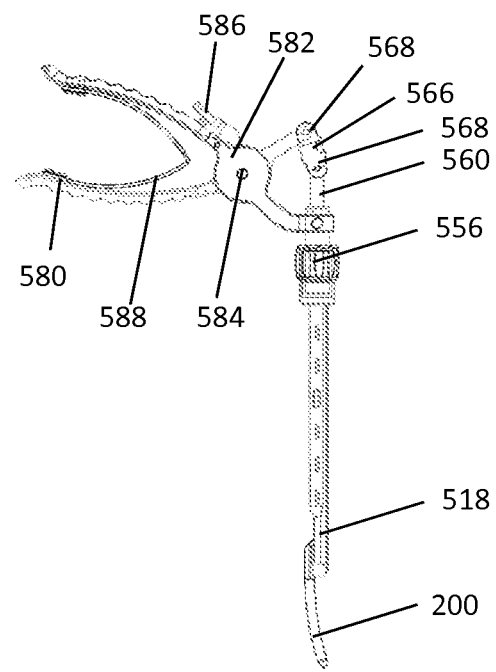
Figure 37C:
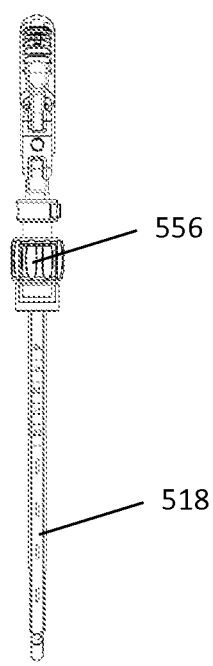
Figure 37D:
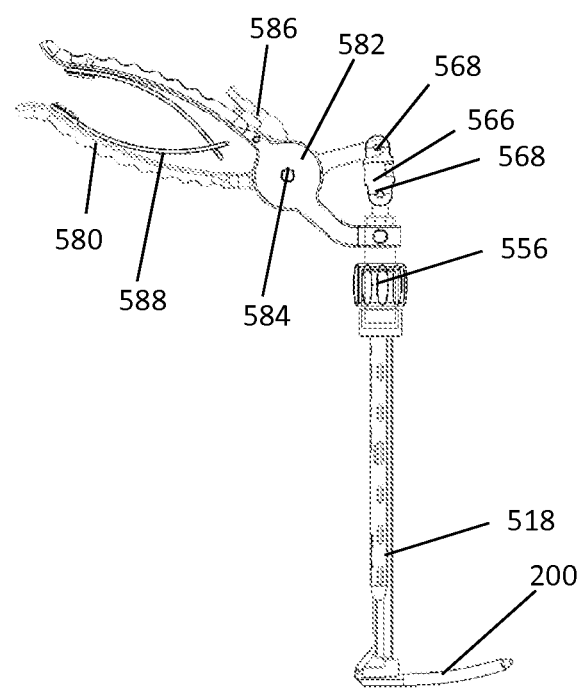

Referring now to FIGS. 37A-37H, an alternative embodiment of a stabilization member insertion device 500 is shown, which may be suitable for use, for example, in an open or mini-open surgical procedure. Insertion device 500 is substantially similar to insertion devices 300 and 400 except that the handles 480 are coupled to the pusher member 560 with an alternative linking member 566. FIG. 37A shows a front view and FIG. 37B shows a side view of the insertion device 500 in the first, insertion orientation. The insertion device 500 may include an outer guide tube 518 having the pusher member 560 and/or pin assembly including pin 558 extending therethrough. The guide tube 518 may include a series of markings, as shown in FIG. 37A, to identify depth of the instrument within the surgical opening, for example. FIGS. 37C and 37D show a front view and side view, respectively, of the insertion device 500 with the stabilization member 200 in the second, articulated orientation.

FIG. 37E shows a side view and FIG. 37G shows a cross-sectional view of the insertion device 500 in the first, insertion orientation, and FIG. 37F shows a side view and FIG. 37G shows a cross-sectional view of the insertion device 500 in the second, articulated orientation. As is evident in FIGS. 37G and 37H, a pin assembly including pin 558 may extending through the outer guide tube 518. The pin assembly including pin 558 may be configured to enable locking and unlocking of the elongate stabilization member 200 to the insertion device 500. As previously described, the thumb nut 556 may be rotated to linearly advance the pin 558, engage the clamping members 510, and lock the stabilization member 200 to the device 500. The pin 558 may unlock the clamping members 510 by rotating the thumb nut 556 in the opposite direction.

The pusher member 560 may be configured to enable pivoting (e.g., from about 0° to) 90° of the elongate stabilization member 200 from the insertion orientation to the final, installation orientation. The pusher member 560 may be advanced linearly to move linking member 562, which is coupled to the clamping members 510. The pusher member 560 may be coupled to the linking member 562 and the linking member 562 to the clamping member 510 with coupling members 564. The pusher member 560 may be advanced using handles 580, which are connected using a ratchet 582 affixed by coupling member 584, which acts as a pivot point. The ratchet 582 may include a uni-directional ratchet, for example, in the shape of a wheel having a plurality of teeth positioned around the periphery. The ratchet 582 may be locked by a locking member 586, for example, having corresponding teeth designed to engage the ratchet 582 when depressed.

One of the handles 580 may be coupled to the pusher member 560 by linking member 566. The other handle 580 may be coupled to a portion of the sleeve or outer guide tube 518. The linking member 566 may be attached to the handle 580 and/or the pusher member 560 by one or more coupling members 568. The coupling members 564, 568, 584, which act as pivot points, may include pins, for example. The linking member 566 may be provided, for example, to assist with disassembly and/or cleaning of the device 500. In addition, the handles 580 may be provided with one or more spring elements 588 to control the pivoting mechanism and allow the handles 580 to maintain an expanded position unless a force is applied. In particular, each handle 580 may include a spring element 588 positioned on an inner surface of the handle 580 and configured to engage another spring element 588 on the opposite handle 580. As shown in FIG. 37B when the handles 580 are expanded apart from one another, the elongate stabilization member 200 is positioned in the insertion orientation with the elongate stabilization member 200 positioned substantially parallel to the guide tube 518 of the insertion device 500. When the handles are squeezed together and closer to one another as shown in FIG. 37D, the pusher member 560 moves linearly causing the linking member 562 to pivot and moving the elongate stabilization member 200 into the installation orientation with the elongate stabilization member 200 positioned substantially perpendicular to the guide tube 518 of the insertion device 500.

Figure 38A:
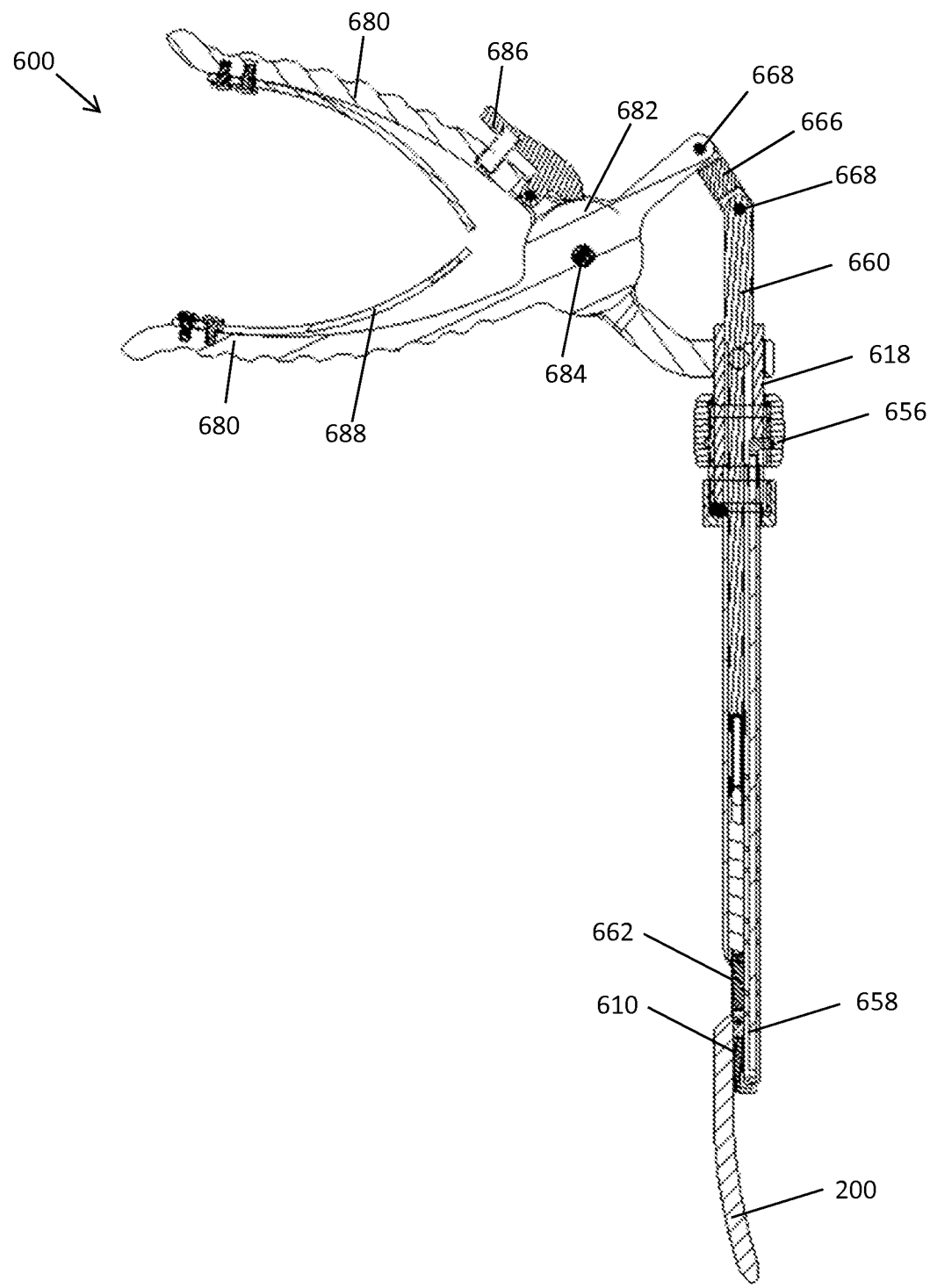

Referring now to FIGS. 38A-38I, an alternative embodiment of a stabilization member insertion device 600 is shown, which may be suitable for use, for example, in an open or mini-open surgical procedure. Insertion device 600 is substantially similar to insertion devices 300, 400, and 500. FIG. 38A depicts a cross-sectional view, FIG. 38B shows a front view, and FIG. 38C shows a side view of the insertion device 600 in the first, insertion orientation. FIGS. 38D and 38E show a front view and side view, respectively, of the insertion device 600 with the stabilization member 200 in the second, implantation orientation.

FIG. 38F shows a side view and FIG. 38H shows a cross-sectional view of the insertion device 600 in the first, insertion orientation, and FIG. 38G shows a side view and FIG. 38I shows a cross-sectional view of the insertion device 600 in the second, articulated orientation. Similar to the other devices described herein, the insertion device 600 may include an outer guide tube 618 having a central longitudinal opening extending from a first end to a second end and including, for example, a series of markings to identify depth of the instrument within the surgical opening. The outer guide tube 618 may house the pusher member 660 and/or pin assembly including pin 658 extending through the central opening. The pin assembly including pin 658 may be configured to enable locking and unlocking of the elongate stabilization member 200 to the insertion device 600, for example, by rotating the thumb nut 656. By rotating thumb nut 656, the pin 658 may be moved linearly to engage or disengage the clamping members 610 to the stabilization member 200. FIGS. 38F and 38G show the pin 658 in the unlocked position such that the clamping members 610 are free to open and close, and FIGS. 38H and 38I show the pin 658 in the locked position such that the clamping members 610 are locked in position to retain the elongate stabilization member 200.

The pusher member 660 may also be advanced linearly by squeezing the handles 680 together. For example, the handles 680 may be squeezed together causing linking member 666 to move pusher member 660 linearly. By moving the pusher member 660 linearly, linking member 662 is caused to pivot and move the elongate stabilization member 200 about 90° relative to its initial position. The handles 680 may be further controlled with a ratchet 682, which pivots about coupling member 684. The ratchet 682 may include a uni-directional ratchet, for example, in the shape of a wheel having a plurality of teeth positioned around the periphery. The handles 680 may be locked in a fixed position relative to one another by a thumb lever or locking member 686, for example.

One of the handles 680 may be coupled to the pusher member 660 by linking member 666, and the other handle 680 may be rigidly affixed to a portion of the sleeve or outer guide tube 618. The linking members 662, 666 may be attached using one or more coupling members 664, 668, for example, such as pins which enable pivoting of the respective linking members 662, 666. In addition, the handles 680 may be provided with one or more spring elements 688 to control the pivoting mechanism and allow the handles 680 to maintain an expanded position unless a force is applied.

While the invention herein disclosed has been described with reference to specific embodiments and applications thereof, numerous modifications and variations can be made thereto by those skilled in the art without departing from the scope of the invention as set forth in the claims.

What is claimed is:

1. A minimally invasive vertebral stabilization system, comprising:
a first anchor deliverable to a vertebral body of a patient through a first opening with at least one extended tab connected thereto, the at least one extended tab defining an open central portion and a central longitudinal axis, wherein the at least one extended tab includes a first extension element integrally connected to the first anchor at a break point;
an elongate stabilization member extending from a proximal end to a distal end; and
a stabilization member insertion device releasably and rotatably linked to the elongate stabilization member, the stabilization member insertion device comprising an outer guide tube, having a longitudinal axis and a central longitudinal opening extending therethrough, a clamping element, and a pin assembly, wherein the pin assembly includes a pin extending through the central longitudinal opening of the outer guide tube, the pin having a first end engaged with an actuation member and a second end configured to engage the clamping element, such that when the actuation member is rotated, the pin linearly moves along the direction of the longitudinal axis and engages a portion of the clamping element,
wherein the elongate stabilization member is deliverable in a first orientation substantially parallel to the central longitudinal axis of the open central portion; and, independent of movement along the central longitudinal axis, the elongate stabilization member is rotatably actuatable by the stabilization member insertion device to extend in a second orientation angled with respect to the first orientation to position the stabilization member in relation to the first anchor,
wherein the elongate stabilization member is cantilevered off the stabilization member insertion device such that at least a portion of the elongate stabilization member is positioned outside the at least one extended tab.

2. The system of claim 1, wherein the outer guide tube having an elongate body extending from a first end to a second end, and
a pusher member extending through the central longitudinal opening of the outer guide tube having a first end connected to a handle and a second end connected to the clamping element, wherein the stabilization member insertion device is configured and dimensioned to be received within the open central portion such that the insertion device is moveable along the central longitudinal axis.

3. The system of claim 2, wherein the elongate stabilization member is releasably clampable to the insertion device between first and second clamping members at a clamping location spaced from a midline of the elongate stabilization member.

4. The system of claim 3, wherein the first clamping member includes a first generally cylindrical protrusion insertable into a distal portion of the insertion device and the second clamping member includes a second generally cylindrical protrusion insertable into the distal portion of the insertion device, and wherein the first and second clamping members are coupled by a pin extending through a first and second opening in the first and second clamping members, respectively.

5. The system of claim 1, wherein the proximal end of the elongate stabilization member is not contained within the open central portion in the first orientation.

6. The system of claim 1, wherein the at least one extended tab includes a first extension element connected to the first anchor at a break point and a second extension element connected to the first extension element.

7. The system of claim 1, wherein the at least one extended tab includes a pair of diametrically opposed extended tabs defining opposed longitudinal openings, the longitudinal openings providing lateral access to the open central portion.

8. The system of claim 7, wherein a portion of the elongate stabilization member is extendable through the longitudinal openings.

9. A minimally invasive vertebral stabilization system, comprising:
 an anchor deliverable to a vertebral body of a patient with at least one extended tab connected thereto, the at least one extended tab including a first extension element connected to the first anchor at a break point and a second extension element connected to the first extension element, and the at least one extended tab defining an open central portion and a central longitudinal axis;
 an elongate stabilization member extending from a proximal end to a distal end; and
 a stabilization member insertion device releasably and rotatably linked to the proximal end of the elongate stabilization member, the stabilization member insertion device including:
  an outer guide tube having an elongate body extending from a first end to a second end and having a central longitudinal opening extending therethrough,
  a clamping element,
  a pin assembly extending through the central longitudinal opening of the outer guide tube, the pin assembly having a first end engaged with an actuation member and a second end configured to engage the clamping element, such that when the actuation member is rotated, the pin assembly linearly moves along the direction of the longitudinal axis and engages a portion of the clamping element, and
  a pusher member extending through the central longitudinal opening of the outer guide tube having a first end connected to a handle and a second end connected to the clamping element,
  wherein the stabilization member insertion device is configured and dimensioned to be received within the open central portion such that the insertion device is moveable along the central longitudinal axis,
 wherein the elongate stabilization member is cantilevered off the stabilization member insertion device such that at least a portion of the elongate stabilization member is positioned outside the second extension element of the at least one extended tab, and
 wherein the elongate stabilization member is deliverable in a first orientation substantially parallel to the central longitudinal axis of the open central portion; and, independent of movement along the central longitudinal axis, the elongate stabilization member is rotatably actuatable by the stabilization member insertion device to extend in a second orientation angled with respect to the first orientation to position the stabilization member proximate to the anchor.

\* \* \* \* \*